United States Patent
Wang et al.

(10) Patent No.: US 7,700,584 B2
(45) Date of Patent: Apr. 20, 2010

(54) CURCUMOL DERIVATIVES, THE COMPOSITIONS CONTAINING THE SAID DERIVATIVES, AND THE USE OF THE SAME IN THE MANUFACTURE OF MEDICAMENTS

(75) Inventors: Shulong Wang, Hang Zhou (CN); Dianwu Guo, Hang Zhou (CN); Zhaoke Meng, Hang Zhou (CN)

(73) Assignee: Hangzhou Minsheng Pharmaceuticals Co., Ltd., Hangzhou (CN)

( * ) Notice: Subject to any disclaimer, the term of this patent is extended or adjusted under 35 U.S.C. 154(b) by 465 days.

(21) Appl. No.: 11/568,770

(22) PCT Filed: May 26, 2005

(86) PCT No.: PCT/CN2005/000730

§ 371 (c)(1),
(2), (4) Date: Nov. 7, 2006

(87) PCT Pub. No.: WO2005/116036

PCT Pub. Date: Dec. 8, 2005

(65) Prior Publication Data

US 2007/0191360 A1     Aug. 16, 2007

(30) Foreign Application Priority Data

May 26, 2004   (CN) .................. 2004 1 0044336

(51) Int. Cl.
| A61K 43/00 | (2006.01) |
| A61K 43/16 | (2006.01) |
| C07D 311/94 | (2006.01) |
| C07D 265/30 | (2006.01) |
| C07D 401/00 | (2006.01) |

(52) U.S. Cl. ............... 514/217.03; 514/232.8; 514/241; 514/254.11; 514/256; 514/320; 514/321; 514/359; 514/383; 514/397; 514/422; 549/9; 549/28; 549/60; 549/332; 549/333; 549/346; 549/386; 544/106; 544/148; 544/150; 544/242; 544/333; 544/335; 544/378; 546/192; 546/196; 546/197; 548/253; 548/266.4; 548/311.4; 548/311.7; 548/525; 548/528; 540/596

(58) Field of Classification Search ............... 549/386; 548/250, 253, 260, 266.4, 311.4, 311.7, 525, 548/528; 514/217.03, 232.8, 241, 254.11, 514/256, 320, 321, 359, 383, 397, 422, 450, 514/455

See application file for complete search history.

(56) References Cited

U.S. PATENT DOCUMENTS 3,935,253 A * 1/1976 Naegeli ............... 549/386
4,003,951 A * 1/1977 Naegeli ............... 568/819

OTHER PUBLICATIONS

"Structure of curcumol", see "Chemical & Pharmaceutical Bulletin" vol. 13, No. 12, 1965, p. 1484-1485.
"Structure of curcumol", see "Chemical & Pharmaceutical Bulletin" vol. 16, No. 1, 1968, p. 39-42.
"A series of sesquiterpenes with a 7 a-isopropyl side chain and related compounds isolated from Curcuma wenyujin", see "Chemical & Pharmaceutical Bulletin" vol. 39, No. 4, 1991, p. 843-853.
"Structure of curcumol", see "Chemical & Pharmaceutical Bulletin" vol. 14, No. 11, 1966, p. 1241-1249.
"The absolute stereostructure of curcumol isolated from Curcuma wenyujin", see "Chemical & Pharmaceutical Bulletin" vol. 32, No. 9, 1984, p. 3783-3786.

* cited by examiner

*Primary Examiner*—Janet L. Andres
*Assistant Examiner*—Raymond Covington
(74) *Attorney, Agent, or Firm*—Yuan Qing Jiang

(57) ABSTRACT

The present invention provides curcumol derivatives of the following formula (I) or pharmaceutical acceptable salts thereof:

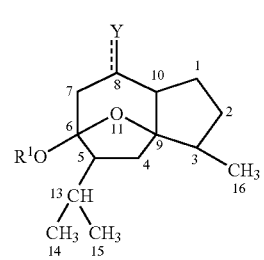

wherein, Y is selected from the group consisting of =$CHR^2$, —$CH_2R^2$, =O,

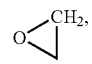

—OH or —$OR^1$; $R^1$ is selected from H, R, RCO or $HO_3S$; and R is selected from the group consisting of H; saturated or unsaturated linear $C_{1-10}$ hydrocarbon group and the like; $R^2$ is selected from the group consisting of F; Cl; Br; I; H; —OH; —OR; —$HSO_3$ and the like; with the proviso that both $R^1$ and $R^2$ are not H. The present invention also provides anti-tumor or antiviral pharmaceutical compositions comprising said derivatives or pharmaceutical acceptable salts thereof. The present invention further provides the use of said derivatives or pharmaceutical acceptable salts thereof in the preparation of a medicament for prophylaxis and/or treatment tumor or an antiviral medicament.

14 Claims, 1 Drawing Sheet

CURCUMOL DERIVATIVES, THE COMPOSITIONS CONTAINING THE SAID DERIVATIVES, AND THE USE OF THE SAME IN THE MANUFACTURE OF MEDICAMENTS

TECHNICAL FIELD

The present invention relates to curcumol derivatives, compositions containing the said derivatives, and use of the same in the manufacture of anti-tumor and antiviral medicaments.

TECHNICAL BACKGROUND

Zedoaria is a Zingliberaceae plant *Curcuma zedoaria*. The rhizome of *Curcuma kwangsiensis* S. Lee et C. F. Liang or *curcuma aromatica* Salisb (RADIX CURCUMAE) is bitter and acrid in tastep, warm-natured and is able toregulate Qi and promote blodd circulation, remove food retention and alleviate pain. It mainly cures abdominal mass, congestion and amenorrhea, food retention and gas pains. Its valotile oil can be used to treat uterine cervix cancer. It has been included in the Chinese pharmacopeia of 1977 (Page 463). The active component is the volatile oil with the content being 1%-2.5%. The main components in the oil are a variety of sesquiterpenes: curzerenone, curdione, neocurdione, epicurcumol, curzerene, curcumol, isocurcumol, procurcumenol, dehydrocurdione and the like, totally about more than twenty chemical components. Curcumol and curdione are the mainly effective components of curcumol oil for treating cancer.

Curcumol, also known as curcumenol and turmerol, molecular formula: $C_{15}H_{24}O_2$, molecular weight: 236.34, [CAS] 4871-97-0, melting point: 141-142° C., has the following structure formula:

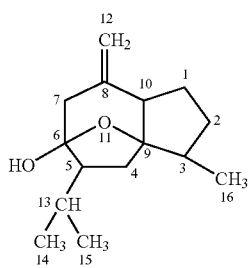

Subcutaneously injecting of 75 mg/Kg curcumol exhibited a high inhibition rate against mouse sarcoma 37, uterine cervix cancer, and Ehrlich's ascites carcinoma (EAC). In patients whose tumor was remarkably diminished, it could be observed that fibrocytes around the tumor tissue significantly increased. They have a inner layer of lymphocyte. Immune response, for example, phagocytes surrounding the tumor cells, was also observed.

Curcumol has not only a significant anti-tumor effect, but also the effects of promoting immune response, increasing leucocytes, protecting the liver, preventing kidney failure, anti-thromb, antibiosis, and the like. At the same time, it has no observable toxicity, and its side effect is relatively low.

Therefore, curcumol is a very useful natural drugs. However, it exists the following deficiencies:
1. Poor water solubility, difficult to produce stable medicament liquid with an appropriate concentration.
2. Severe pain when being topically injected or injected into the neoplasma. Chest distress, flush and dyspneic respiration and other symptoms will occur when it is injected too fast.
3. The variety of tumors to be treated is limited.
4. Strong toxicity.

Although the total effective rate reaches more than 70% with respect to earlier period uterine cervix cancer, there still exists the possibility for further improving the drug effect.

CONTENTS OF THE INVENTION

An object of the invention is to provide curcumol derivatives having good stability and solubility, better partition coefficient between lipo phase and aqueous phase, anti-tumor activity and broader spectrum for anti-tumor, better drug effect and less toxicity.

Another object of the invention is to provide a pharmaceutical composition comprising the curcumol derivatives.

A further object of the invention is to provide the use of the curcumol derivatives in the manufacture of medicaments.

The present invention relates to a curcumol derivative with formula I, or a pharmaceutically acceptable salt thereof

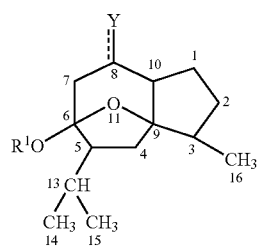

I wherein, Y is selected from the group consisting of $=CHR^2$, $—CH_2R^2$, $=O$,

—OH and —OR$^1$;

R$^1$ is selected from the group consisting of H, R, RCO and HO$_3$S;

R is selected from the group consisting of H; saturated or unsaturated linear $C_{1-10}$ hydrocarbon group; saturated or unsaturated branched $C_{3-10}$ hydrocarbon group; $C_{3-10}$ hydrocarbon ether; $C_{3-10}$ hydrocarbon sulfide; saturated or unsaturated, $C_{3-8}$ cyclic hydrocarbon group optically substituted by one or more substitutents selected from the group consisting of nitro, sulfonic group, halogen atom and hydroxyl group; or $C_{6-12}$ aryl group;

$Y^1NY^2$, $Y^1CONY^2$, wherein $Y^1$ is H or $C_{1-8}$ and $Y^2$ is $C_{1-8}$; being selected from the following heterocycles:

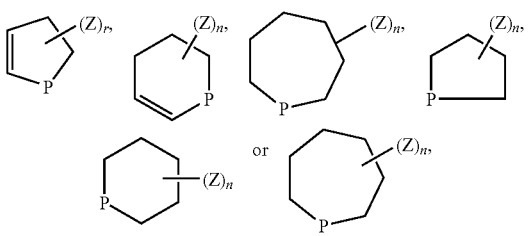

wherein, P is S, O or N, and Z is one or more substitutents selected from the group consisting of H, hydroxy group, saturated or unsaturated linear $C_{1-6}$ hydrocarbon group, saturated and unsaturated branched $C_{3-6}$ hydrocarbon group, and n=1-3; or $R^1$ is the acyl of coffeic acid, gambogic acid, of isogambogic acid, of neogambogic acid or of glycyrrhizic acid;

$R^2$ is selected from the group consisting of F; Cl; Br; I; H; —OH; —OR; —HSO$_3$; —NO$_3$; RNH— and R'NR'', wherein, R' and R'' may be the same or different, and each is selected from the group consisting of the groups defined in R and H$_2$NRNH—;

or $R^2$ is selected from the group consisting of pyridyl, pyrrolyl, imidazolyl, triazolyl, tetrazolyl, dioxazolyl, dioxadiazolyl, piperidyl,

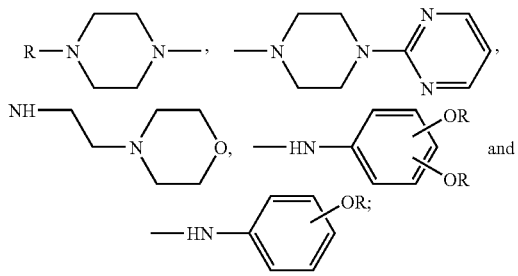

With the proviso that both $R^1$ and $R^2$ are not H,

Y . . . is a single bond, when Y is —OH or —OR$^1$,

When Y is —CHR$^2$, the derivative has the general formula II:

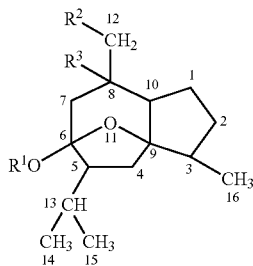

wherein, $R^1$ and $R^2$ are defined as above, $R^3$ is selected from the group consisting of F; Cl; Br; I; H; —OH; —HSO$_3$; —NO$_3$; —RNH and R'NR'', wherein, R' and R'' may be the same or different, and each is selected from the group consisting of the one for defining R; or R' and R'' may independently be H$_2$NRNH—;

or $R^2$ is selected from the group consisting of pyridyl, pyrrolyl, imidazolyl, triazolyl, tetrazolyl, dioxazolyl, dioxadiazolyl, piperidyl,

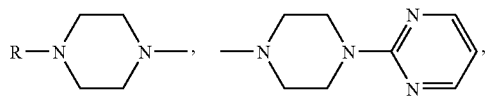

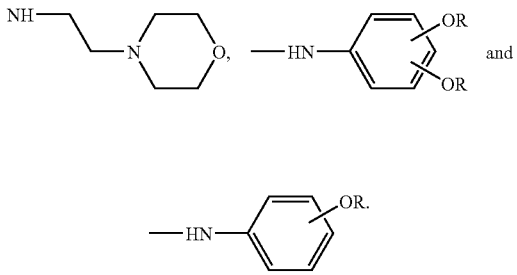

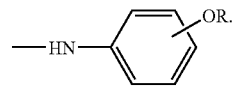

In a preferred embodiment, the aryl group is preferably selected from the group consisting of Ar—, ArCH$_2$—, ArCH$_2$CH$_2$—, and CH$_3$ArCH$_2$CH$_2$—, Ar— is phenyl, or phenyl group substituted with F, Cl, Br, I, nitro, sulfonic acid group or 1-3 hydroxy groups. When Y is =CHR$^2$, $R^2$ is preferably H; and $R^1$ is preferably HO$_3$S, propionyl, butyryl, isobutyryl or benzoyl.

In another preferred embodiment, when Y is =CHR$^2$, $R^2$ is H, and $R^1$ is HO$_3$S or NaO$_3$S.

The most preferable curcumol derivatives or pharmaceutically acceptable salts are selected from the group consisting of the following compounds:

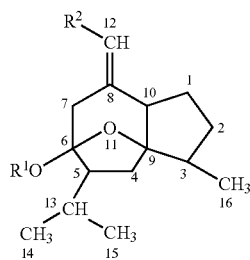

| No. | Name of the compounds | $R^1$ | $R^2$ |
|---|---|---|---|
| 1 | Curcumol acetate | CH$_3$CO— | H |
| 2 | Curcumol butyrate | CH$_3$CH$_2$CH$_2$CH$_2$C— | H |
| 3 | Curcumol isobutyrate | (CH$_3$)$_2$CH$_2$CO— | H |

-continued

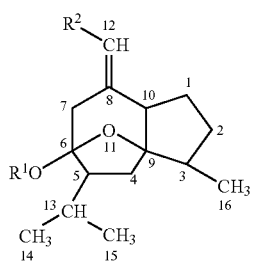

III

| No. | Name of the compounds | R¹ | R² |
|---|---|---|---|
| 4 | Curcumol benzoate | C₆H₅—CO— (phenyl-CO) | H |
| 5 | Curcumol p-hydroxy aniline | H | —HN—C₆H₄—OH (p-hydroxy) |
| 6 | Curcumol p-hydroxy aniline hydrochloride | H | —HN—C₆H₄—OH (p-hydroxy) |
| 7 | Curcumol piperazine | H | piperazinyl (HN-N) |
| 8 | Curcumol piperazine hydrochloride | H | piperazinyl (HN-N) |
| 9 | Curcumol heterocyclyl ethylamine | H | NH—CH₂CH₂—N(morpholine) |
| 10 | Curcumol heterocyclyl ethylamine hydrochloride | H | NH—CH₂CH₂—N(morpholine) |
| 11 | 3,4-dihydroxy aniline | H | —HN—C₆H₃(OH)₂ (3,4-diOH) |
| 12 | 3,4-dihydroxy aniline hydrochloride | H | —HN—C₆H₃(OH)₂ (3,4-diOH) |
| 13 | Curcumol n-butyl amine | H | $CH_3CH_2CH_2CH_2NH-$ |
| 14 | Curcumol n-butyl amine hydrochloride | H | $CH_3CH_2CH_2CH_2NH-$ |
| 15 | Curcumol t-butyl amine | H | $(CH_3)_3CNH-$ |
| 16 | Curcumol t-butyl amine hydrochloride | H | $(CH_3)_3CNH-$ |
| 17 | Curcumol monobromide | H | —Br |
| 18 | Curcumol monohydroxy compound | H | —OH |
| 19 | Curcumol mononitrate | H | —NO₃ |
| 20 | Curcumol sulfonate | $HSO_3-$ | H |
| 21 | Curcumol sodium sulfonate | $NaSO_3-$ | H |

-continued

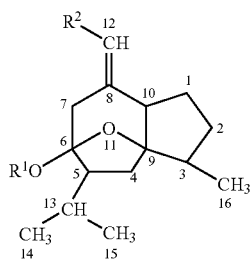

III

| No. | Name of the compounds | R¹ | R² |
|---|---|---|---|
| 22 | Curcumol acrylate | $CH_2=CHCO-$ | H |
| 23 | Curcumol diethanolamine | H | $(CH_3CH_2)_2N-$ |
| 24 | Curcumol diethanolamine hydrochloride | H | $(CH_3CH_2)_2N-$ |
| 25 | Curcumol methyl ether | $CH_3$ | H |
| 26 | Curcumol methyl ether bromide | $CH_3$ | $-Br$ |
| 27 | Curcumol methyl ether n-butyl amine | $CH_3$ | $CH_3CH_2CH_2CH_2NH-$ |
| 28 | Curcumol methyl ether n-butyl amine hydrochloride | $CH_3$ | $CH_3CH_2CH_2CH_2NH-$ |
| 29 | Curcumol ethyl ether nitrate | $CH_3CH_2-$ | $-NO_3$ |

Alternatively, the curcumol derivatives or pharmaceutically acceptable salts thereof have the following structures:

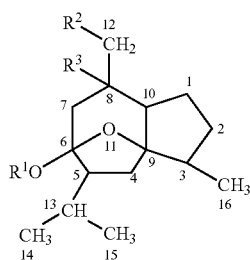

II wherein, the groups in the formula are defined as follows:

| No. | Name of the compounds | R¹ | R² | R³ |
|---|---|---|---|---|
| 30 | Curcumol dibromide | H | $-Br$ | $-Br$ |
| 31 | Curcumol dinitrate | H | $-NO_3$ | $-NO_3$ |
| 32 | Curcumol dihydroxy compound | H | $-OH$ | $-OH$ |
| 33 | hydrogenated curcumol derivative | H | H | H |
| 34 | Curcumol monobromide without double bond | H | H | $-Br$ |
| 35 | Curcumol monohydroxy compound without double bond | H | H | $-OH$ |
| 36 | Curcumol mononitrate without double bond | H | H | $-NO_3$ |
| 37 | Curcumol p-hydroxy aniline without double bond | H | H | $-HN-\text{C}_6\text{H}_4-OH$ |
| 38 | Curcumol p-hydroxy aniline hydrochloride without double bond | H | H | $-HN-\text{C}_6\text{H}_4-OH$ |

-continued

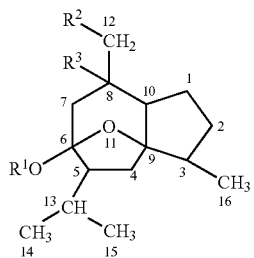

II wherein, the groups in the formula are defined as follows:

| No. | Name of the compounds | R¹ | R² | R³ |
|---|---|---|---|---|
| 39 | Curcumol bis (p-hydroxy aniline) | H | —HN—⟨benzene⟩—OH | —HN—⟨benzene⟩—OH |
| 40 | Curcumol bis (p-hydroxy aniline) hydrochloride | H | —HN—⟨benzene⟩—OH | —HN—⟨benzene⟩—OH |
| 41 | Curcumol bispiperazine | H | HN⟨piperazine⟩N— | HN⟨piperazine⟩N— |
| 42 | Curcumol bispiperazine hydrochloride | H | HN⟨piperazine⟩N— | HN⟨piperazine⟩N— |
| 43 | Curcumol piperazine without double bond | H | H | HN⟨piperazine⟩N— |
| 44 | Curcumol piperazine hydrochloride without double bond | H | H | HN⟨piperazine⟩N— |
| 45 | Curcumol methyl ether n-butyl amine without double bond | $CH_3$ | H | $CH_3CH_2CH_2CH_2NH$ |
| 46 | Curcumol methyl ether n-butyl amine hydrochloride without double bond | $CH_3$ | H | $CH_3CH_2CH_2CH_2NH$ |

In another variant, the curcumol derivatives or the pharmaceutically acceptable thereof have the following structures:

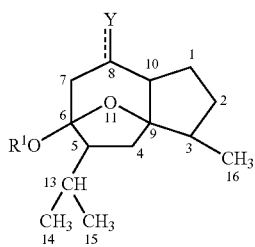

I

Wherein, the groups in the formula are defined as follows:

| No. | Name of the compounds | R¹ | Y |
|---|---|---|---|
| 47 | Curcumol epoxy compound | H | $O\!\!\triangleleft\!\!{}^{CH_2}$ |
| 48 | Curzerenone | H | O |
| 49 | Curzerenone acetate | $CH_3CO—$ | O |

In another most preferred embodiment of the present invention, the most preferred curcumol derivatives or pharmaceutical salts thereof are selected from the following compounds:

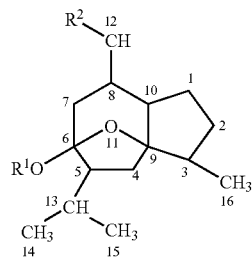

| | | |
|---|---|---|
| curcumol p-hydroxy aniline | H | 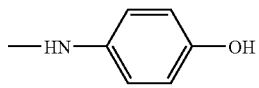 |
| curcumol p-hydroxy aniline hydrochloride | H | 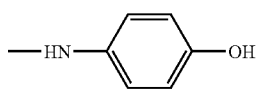 |
| Curcumol propionate | CH₃CH₂CO— | H |
| Curcumol butyrate | CH₃CH₂CH₂CO— | H |
| Curcumol isobutyrate | (CH₃)₂CH₂CO— | H |
| Curcumol benzoate | 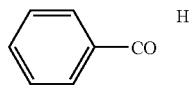 | H |
| Curcumol monobromide | H | —Br |
| Curcumol sulfonate | HSO₃— | H |
| Curcumol sodium sulfonate | NaSO₃— | H |
| Curcumol pipearzine | H |  |
| Curcumol pipearzine hydrochloride | H | 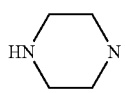 |
| Curcumol n-butyl amine | H | CH₃CH₂CH₂CH₂NH— |
| Curcumol n-butyl amine hydrochloride | H | CH₃CH₂CH₂CH₂NH— |
| Curcumol t-butyl amine | H | (CH₃)₃CNH— |
| Curcumol t-butyl amine hydrochloride | H | (CH₃)₃CNH— |

The present invention also provides an anti-tumor or anti-viral pharmaceutical composition comprising a pharmaceutically effective amount of the afore-mentioned curcumol derivatives or the pharmaceutical acceptable salts thereof, and a pharmaceutically acceptable excipient and/or an additive.

The present invention further provides a use of the afore-mentioned curcumol derivatives or the pharmaceutical acceptable salts thereof in the manufacture of medicaments for treating and/or preventing tumor.

The present invention also provides a use of the afore-mentioned curcumol derivatives or pharmaceutical acceptable salts thereof in the manufacture of anti-viral medicaments. The virus is selected from the group consisting of HIV virus, influenza virus, hepatitis virus and herpes virus.

Curcumol is a component of oleum curcumae wenchowensis, whose content is relatively high. After purifying the commercially available oleum curcumae wenchowensis, curcumol is obtained with relatively high purity (the purity can be higher than 75%, and if necessary, the purity can reach more than 99%). The curcumol of relatively high purity is used as a starting material to be structurally modified. The general methods for the preparation of curcumol derivatives are introduced as follows:

Preparing Hydrogenated Curcumol Derivative

Curcumol was dissolved in an appropriate organic solvent (such as methanol and the like). A small amount of hydrogenation catalyst (e.g., palladium on carbon, and the like) was added. Hydrogen gas was introduced at room temperature, under normal pressure with vigorous stirring to provide a curcumol derivative in which the double bond between 8- and 12-position is hydrogenated.

Preparing the Ester of Curcumol (the Hydroxy Group at ⁶C)

Due to the presence of a hydroxy group at ⁶C of curcumol, curcumol has the general propertiess possessed by alcohols. The esters of curcumol thus can be prepared by general methods: for example, curcumol as a starting material was dissolved in an appropriate organic solvent (for example, isopropyl ether, DMF, dioxane, toluene, dichlormethane, chloroform, acetic acid, and the like), and reacted with carboxylic acid in the presence of a catalyst (e.g., p-toluenesulfonic acid, the complex of dimethylamine sulfonyl chloride with dimethylamine and DMAP, the complex of diphenylamine with DPAT, the complex of DMAP with DPC, organo-titanium, p-toluenesulfonic acid, and the like); or reacted with acyl chloride in the presence of acid binding agents (for example, pyridine, triethylamine, and the like); or reacted with acid anhydride under reflux, to provide the corresponding ester of curcumol. Then after separation and purification treatment, the ester of curcumol in relatively high purity was obtained. Unless indicated otherwise, in the following schemes, "r.t." represents "room temperature", "hr" represents "hours".

1. The Esterification of Curcumol with Acyl Chloride

Curcumol was dissolved in chloroform and reacted with equal amount of mole or an excess amount of acyl chloride in the presence of acid binding agents (e.g., excessive amount of triethylamine) for several hours at room temperature or under reflux, the corresponding ester of curcumol (R in the following formula is defined as above) was obtained:

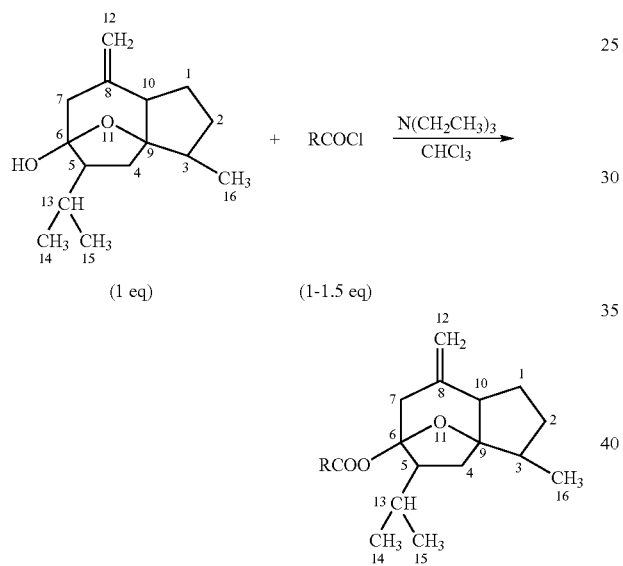

2. The Esterification of Curcumol with Acid Anhydride

Curcumol was dissolved in carboxylic acid (generally acetic acid) and refluxed with an excess amount of acid anhydride for several hours. The ester of curcumol corresponding to the acid anhydride was obtained (R in the following formula is defined as above):

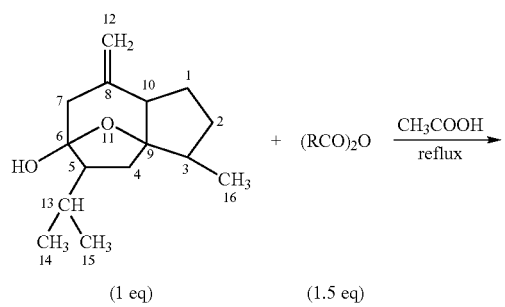

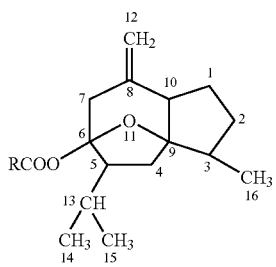

3. The Esterification of Curcumol with Organic Acid in the Presence of Organo-Titanium Catalyst Curcumol was dissolved in dichlormethane, and carboxylic acid and curcumol in substantially equal moles were reacted at room temperature in the presence of organo-titanium reagent as a catalyst and trimethylchlorosilane as a cocatalyst, and in the presence of equal mole of acid anhydride as a dehydrating agent, to provide the corresponding ester of curcumol with high yields (in the following formula, $R^1$ is R, and R is defined as above, $R^2OH$ is curcumol):

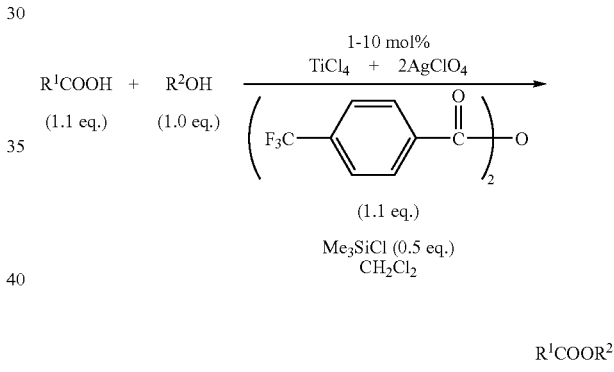

4. The Esterification of Curcumol with Organic Acid Under the Catalysis of DMAP and DPC Curcumol was dissolved in dioxane and reacted with a slight excess of carboxylic acid at 70° C. for 100 hours in the presence of the catalysts DMAP and DPC, to afford the corresponding the ester of curcumol with high yield (R in the following formula is defined as above):

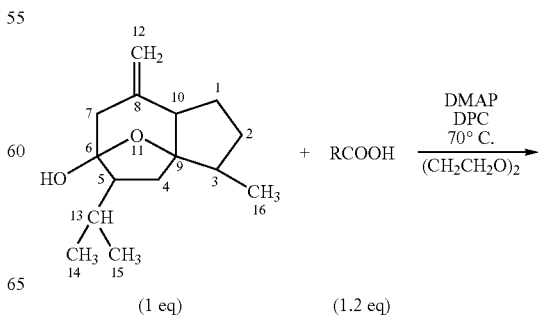

-continued

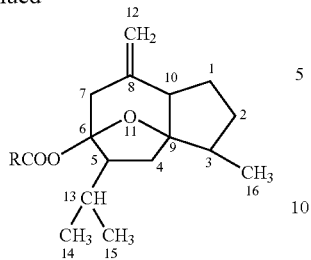

5. The Esterification of Curcumol with Organic Acid Catalyzed by p-toluenesulfonic Acid Curcumol was dissolved in toluene, and reacted with an excess of carboxylic acid under reflux in the presence of the catalyst p-toluenesulfonic acid while the resulting water was separated, to afford the corresponding ester of curcumol (R in the following formula is defined as above):

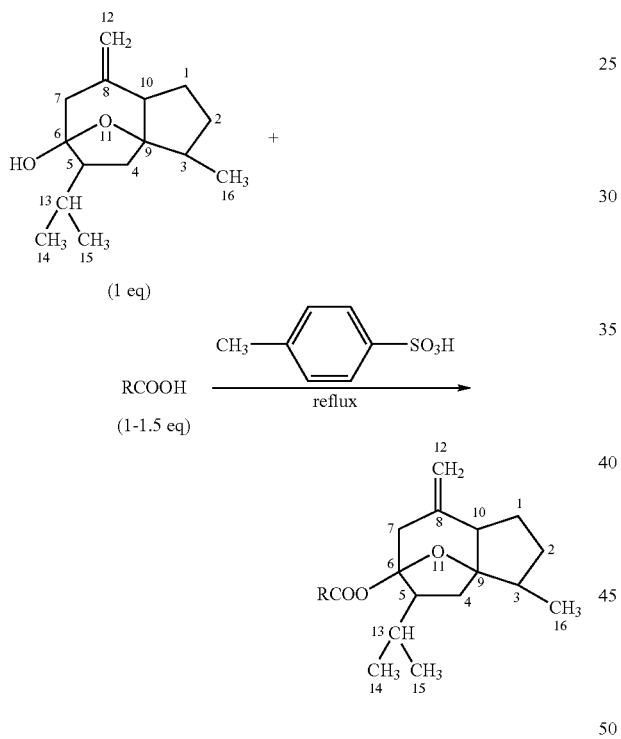

6. Curcumol was dissolved in an appropriate organic solvents (e.g., DMF, ethyl acetate or pyridine, etc.), and reacted with thionyl dichloride. After reacting, the mixture was treated with an alkaline solution to afford curcumol sulfate:

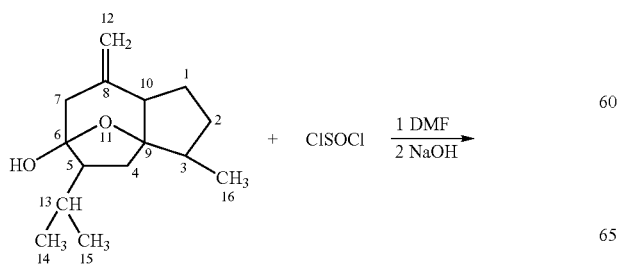

-continued

Similarly, the above prepared hydrogenated curcumol derivative was used as a starting material and proceeded with the above reaction schemes 1-6 to afford the corresponding esters of hydrogenated curcumol derivatives.

Preparing Curcumol Ether (the Hydroxy Group at $^6$C)

Due to the presence of a hydroxy group at $^6$C of curcumol, curcumol has the general properties of alcohols. Curcumol was dissolved in an appropriate organic solvent (e.g., isopropyl ether, DMF, dioxane, toluene, dichlormethane, chloroform), then was reacted with sulfate ($ROSO_2OR$) or an alkane iodide (RI) in a basic solution to afford the corresponding ethers. After the separation and the purification, the curcumol ether in relatively high purity was obtained.

1. Curcumol was dissolved in isopropyl ether and dichlormethane (R in the following formula was defined as above):

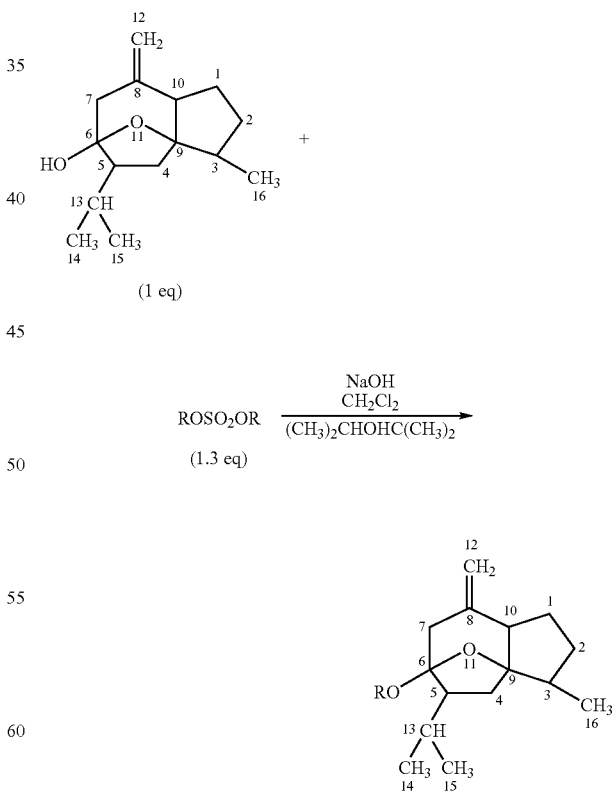

2. Curcumol was dissolved in isopropyl ether and dichlormethane, then was reacted with alkane iodide (R in the following formula was defined as above):

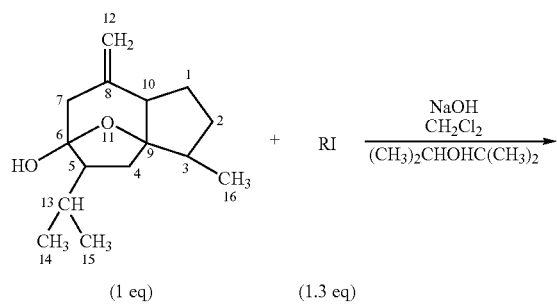

(1 eq)     (1.3 eq)

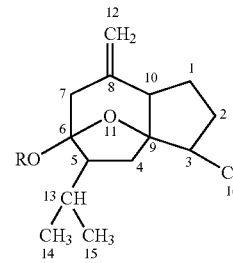

Similarly, the above prepared hydrogenated curcumol derivative was used as a starting material and proceeded with the above reaction schemes 1-2 to afford the corresponding ether of hydrogenated curcumol derivative.

Due to the presence of a double bond between $^8C$ and $^{12}C$ of curcumol, curcumol has the properties, such as being added or being oxidized, the same as those of the other alkene compounds. It may be easily subjected to an addition reaction with halogen, or hydrogen halide to afford curcumol dihalide, or monohalide; or may be reduced by $H_2$, $LiAlH_4$ and the like to afford the hydrogenated curcumol derivatives, or may be added by alkyl epoxy compounds to afford curcumol epoxy compounds; or may be oxidized by oxidizing agents such as potassium permanganate to afford curcumol oxide, dihydroxy compounds.

The halogen atom of the curcumol halide obtained from the above reaction can be replaced by RNH, —R'NR''(R', R'', the same or different, are R), $H_2NRNH$—, wherein R is defined as above, or a heterocyclic group, such as pyridine, pyrole, imidazole, triazole, tetrazole, dioxazole, dioxdiazole, piperidine (as long as there is a nitrogen-hydrogen bond H—N< in the molecule:) or the simple derivatives thereof,

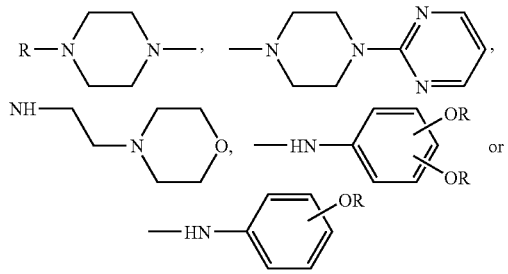

(ortho, meta or para position) (wherein R is defined as above or is H) at room temperature in an appropriate organic solvent to afford the corresponding amine derivatives.

1. The Preparation of the Adduct of Curcumol with Halogen

Curcumol was dissolved in an appropriate organic solvent (such as chloroform, methanol and the like), and was subjected to an addition reaction with halogen ($X_2$, $X_2$ is $Cl_2$, $Br_2$, $I_2$, preferably $Br_2$) at room temperature or below 0° C., to yield a curcumol derivative in which each of $^8C$ and $^{12}C$ were added a halogen atom.

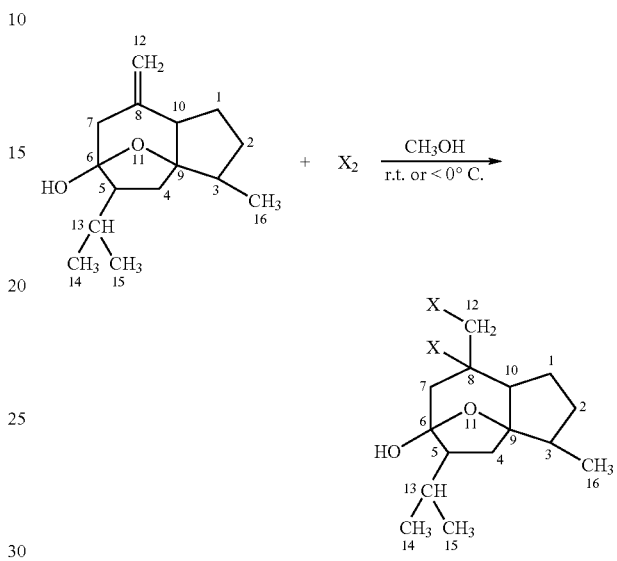

The prepared dihalide tended to eliminate a hydrogen chloride in anhydrous organic solvent under alkaline condition to afford a monohalide in which the double bond between $^8C$ and $^{12}C$ was rebuilt.

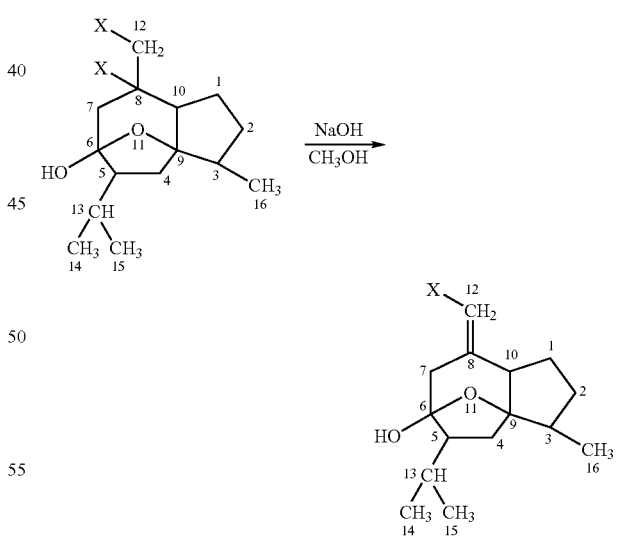

The above prepared curcumol (the hydroxy group at $^6C$) ester, or curcumol (the hydroxy group at $^6C$) ether (R is defined as above, but R does mot include the alkene group containing a double bond), as a starting material, was dissolved in an appropriate organic solvent (such as chloroform, methanol and the like), and was subjected to an addition reaction with halogen at room temperature or below 0° C., to afford the corresponding curcumol derivative in which two halogen atoms are added to $^8C$ and $^{12}C$, respectively. The dihalide was prepared similarly. The prepared dihalide tended to eliminate a hydrogen chloride in anhydrous organic solvent under basic (alkaline) condition to afford a monohalide in which the double bond between $^8C$ and $^{12}C$ was rebuilt.

Halogenation of curcumol ether derivatives and elimination of hydrogen halide:

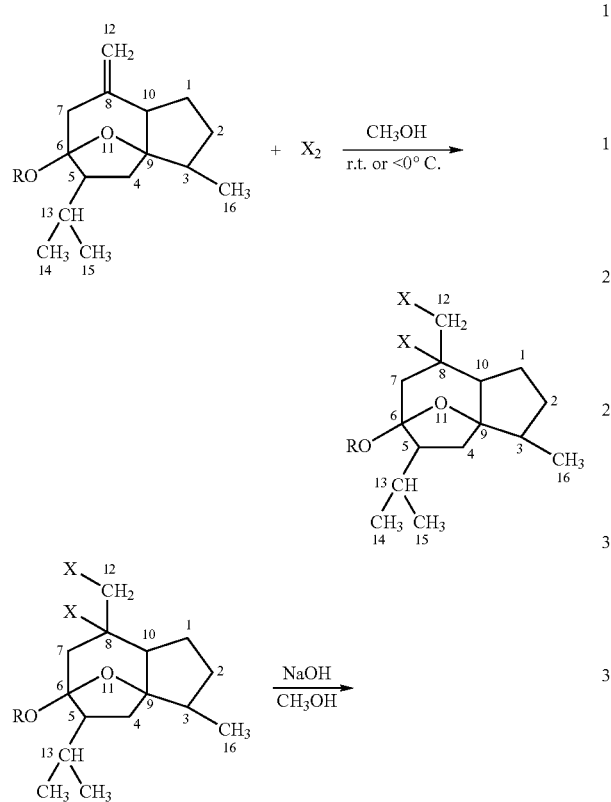

Halogenation of curcumol ester derivatives and elimination of hydrogen halide:

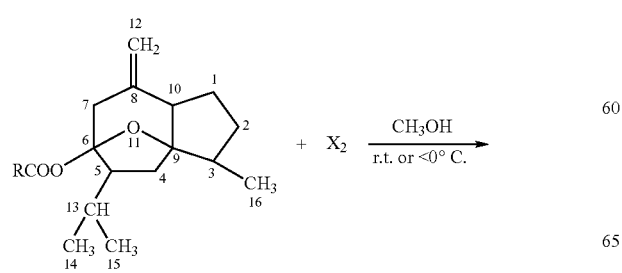

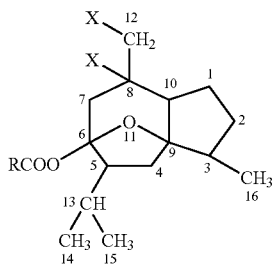

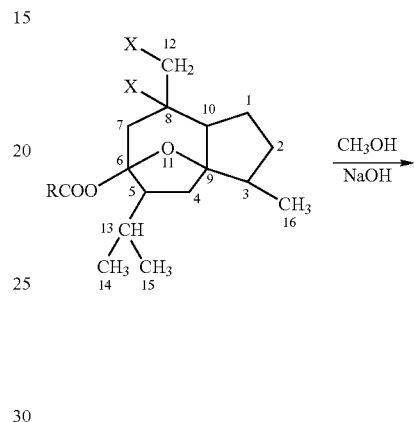

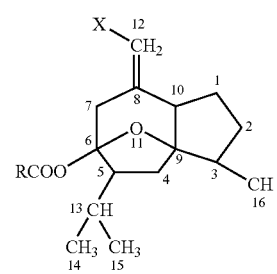

Halogenation of curcumol sulfate derivatives and elimination of hydrogen halide:

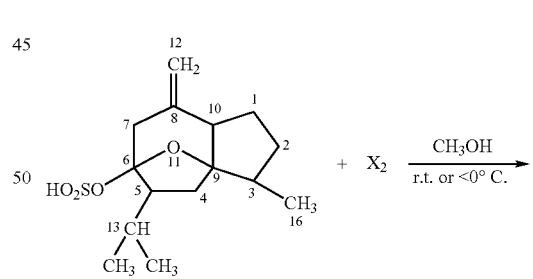

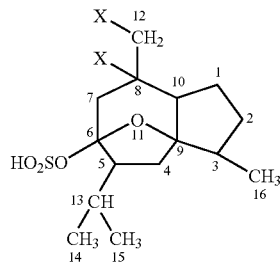

-continued

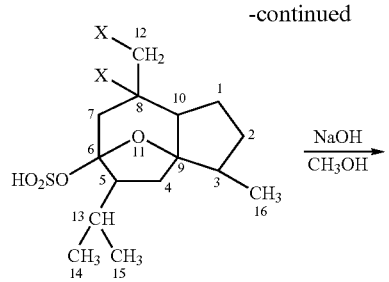

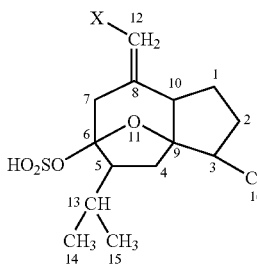

The method for the addition of curcumol to hydrogen halide is similar to that of the addition of curcumol to halogen, with the exception that H was added to $^8C$, while X was added to $^{12}C$.

The above prepared bromide or chloride was dissolved in anhydrous methanol. Fluoride (e.g., $NH_4F$, NaF) was added and reacted at room temperature, yielding the corresponding curcumol fluoride.

The method for the preparation of the curcumol ester halide, in which K contains a double bond, is as follows: curcumol halide was used as a starting material, and then the curcumol ester halide in which R contains a double bond was obtained according to the above esterification method of curcumol.

The Replacement of the Halogen Atom in the Curcumol Halide

One of the above prepared derivative (or curcumol) halides (monohalides or dihalides), mainly bromide, was dissolved in an appropriate anhydrous organic solvent (acetonitrile, tetrahydrofuran and the like), and an excess of (generally 2-3.5 folds in mole) dried amine $R^2$—H (herein $R^2$ is an amine, including nitrogen-containing heterocycle) was added and reacted at room temperature for more than 3 hours. The product was separated by silica gel column or purified by recrystallization to afford the corresponding curcumol amine derivative or the salt thereof ($R^1$ and $R^2$ are defined as above).

Amination of monohalide (The bond between $^8C$ and $^{12}C$ is a double bond) ($R^1$ and $R^2$ are defined as above):

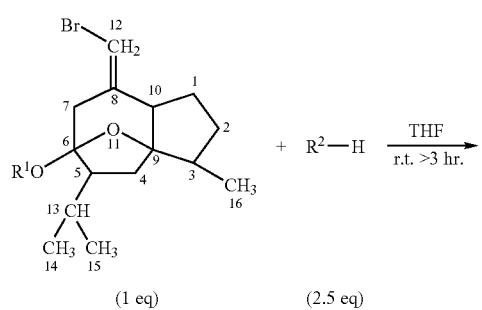

-continued

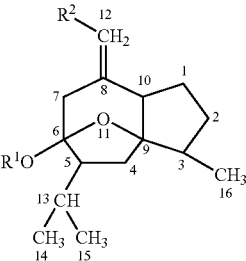

Amination of monohalide (The bond between $^8C$ and $^{12}C$ is a single bond) ($R^1$ and $R^2$ are defined as above):

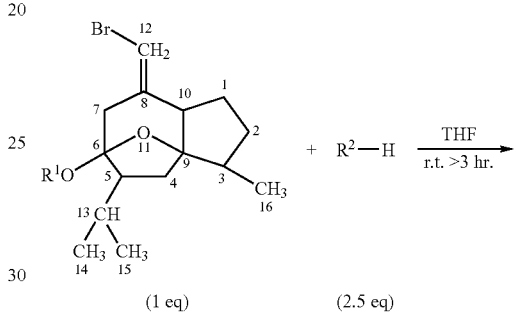

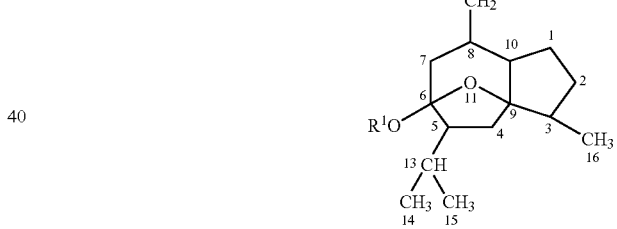

Amination of dihalide: The amination of dihalide provided a large amount of monoaminated compound (formula II) in which the bond between $^8C$ and $^{12}C$ was a double bond and a small amount of diaminated compound (formula III)($R^1$ and $R^2$ are defined as above):

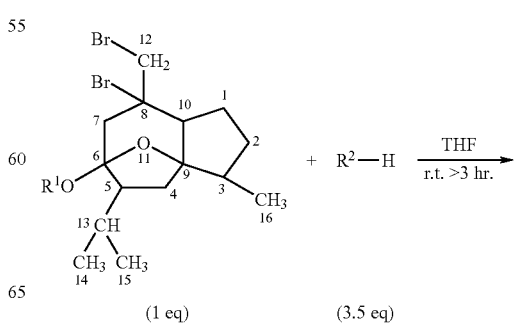

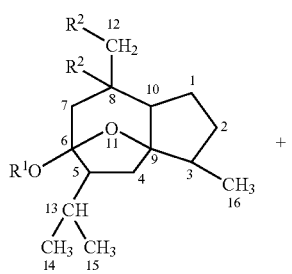

II

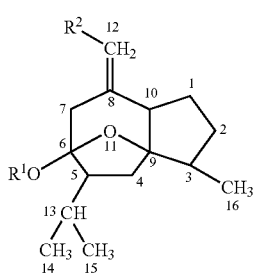

III

Curcumol (or the above prepared curcumol derivatives) monohalide (the bond between $^8C$ and $^{12}C$ is a double bond or a single bond) was dissolved in an appropriate organic solvent (methanol, ethanol, acetone and the like), and reacted with NaOH solution at room temperature. The halogen atom was replaced by a hydroxy group ($R^1$ is defined as above):

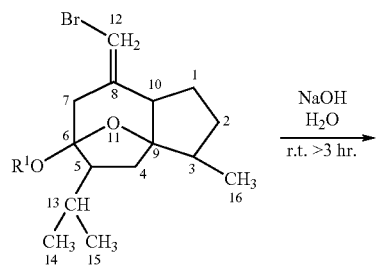

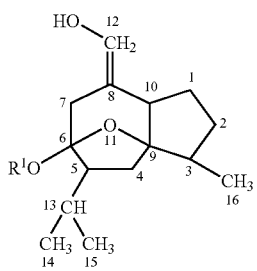

The above reaction provided the curcumol ester derivative at $^{12}C$ of which a hydroxy group was added. The hydroxy group at $^{12}C$ also could be esterified or etherified to afford the corresponding curcumol derivatives ($R^1$ is defined as above):

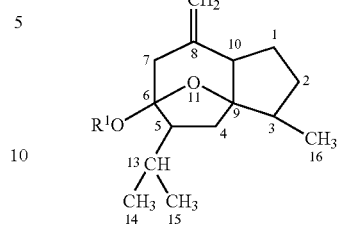

Curcumol halide (mainly bromide) was dissolved in an appropriate solvent (50%-95% methanol solution in water, and the like), and reacted with silver nitrate solution to afford the corresponding curcumol nitrate derivative.

The Preparation of Curcumol Derivatives in Which the Double Bond is Oxidized

The double bond between $^8C$ and $^{12}C$ of curcumol could be oxidized by the oxidizing agents such as potassium permanganate, $H_2O_2$ and the like in an appropriate organic solvent (acetone, acetic acid, and propionic acid, and the like,) to afford curcumol dihydroxy derivative or curzerenone derivative.

Curcumol was oxidized with equal mole of potassium permanganate in the neutral to basic acetone solution to afford curcumol dihydroxy derivative:

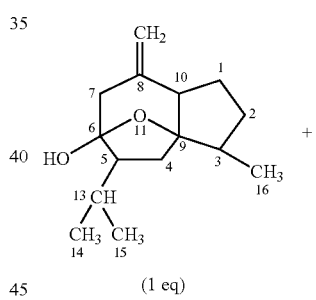

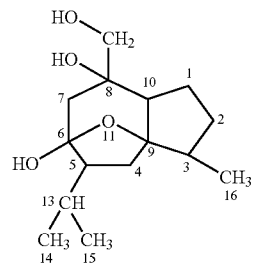

Curcumol was oxidized with the excess amount of the solution of potassium permanganate in acetic acid to afford the curzerenone derivative:

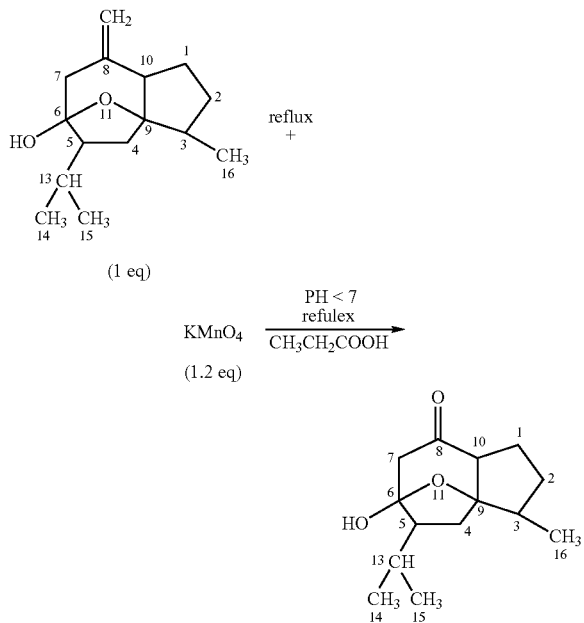

The derivative produced in the reaction can be esterified or etherified to afford the corresponding ester or ether.

The Preparation of Curcumol Epoxy Derivative

Ccurcumol was dissolved in an appropriate organic solvent (chloroform, dichlormethane, and the like), and m-chlorobenzoyl hydroperoxide was added at room temperature. Then the mixture was washed with 5% NAOH solution several times and dried over anhydrous sodium sulfate. The organic solvent was removed under vacuum and the residue was separated by silica gel column to afford the compound of formula (III), wherein Z is

The oxygen ring of the above compound was opened in mild acidic solution to afford the compound of formula (II) wherein $R^2$ is OH and $R^3$ is H. The esterification (or alkylation) of the ring-opening compound (Method 1: the hydroxy group at 6C of curcumol was esterified; Method 2: the hydroxy group at 6C of curcumol was alkylated) afforded the compound of formula (II) wherein $R^3$ is H and $R^2$ is $OR^1$ (wherein $R^1$ is defined as above).

MODE OF CARRYING OUT THE INVENTION

Figure 1:
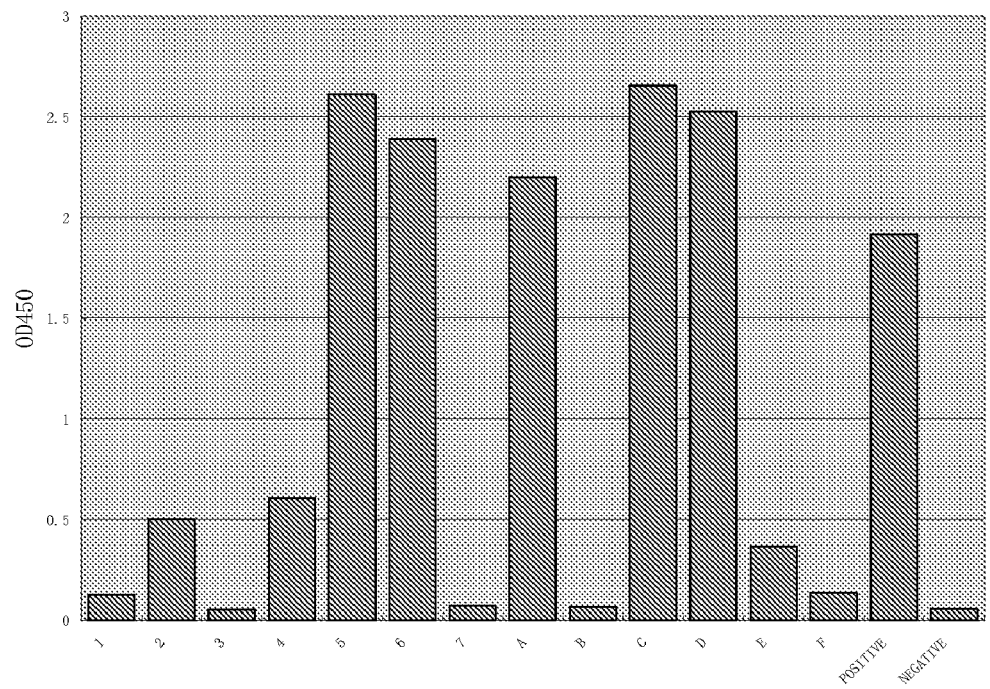
FIG. 1 shows the measured OD450 of HBV e antigen sample upon treatment with curcumol and the compounds according to this invention.

The present invention is further illustrated in combination with the following examples.

Preparation Example 1

Preparing Curcumol Ester (the Hydroxy Group at $^6$C)

(1) 2.48 g (95%, 0.01 mol) of curcumol was dissolved in 50 mL of chloroform. A small amount of anhydrous magnesium sulfate was added and stirred for 3 hours. The magnesium sulfate was removed by filtration. Then a small amount of triethylamine was added, and 1.06 g of acetyl chloride (98%, 0.11 mol) was added dropwise at room temperature. The resulting mixture was stranded for 24 hours and then poured into crushed ice. The solution in chloroform was washed with cold water until the solution was neutral. The aqueous phase was discarded and the organic phase was dried over anhydrous magnesium sulfate. The chloroform was removed under vacuum, to obtain a light yellow product, which was separated with 95:5 petroleum ether (60-90° C.): ethyl acetate and 200-300 mesh silica gel column to afford 1.55 g curcumol acetate (the hydroxyl group in the parent compound was esterified), i.e. the derivative of Formula (III), wherein, $R^1$ is $CH_3CO$ (Compound No. 1), as a colourless to white oil. Yield: 58%, HPLC: 99.5%.

Element analysis using Thermo Finnigam Company (U.S.) FlashEA1112 element analysis apparatus found: C, 73.554%; H, 9.308%; Molecular formula ($C_{17}H_{26}O_3$) calculated: C, 73.344%; H, 9.414%.

Finnigan MAT 8430 Mass spectrometric analysis showed that the molecular weight of the product was 278.

The spectrum showed 17 carbon signals, 26 proton signals, using BrukerACF-300 nuclear magnetic resonance spectrometer and using $CDCl_3$ as a solvent.

This confirmed that the product was Compound No. 1.

(2) 2.48 g (95%, 0.01 mol) of curcumol was dissolved in 50 mL of dioxane, and a small amount of anhydrous magnesium sulfate was added and stirred for 3 hours. The magnesium sulfate was removed by filtration. An appropriate amount of DMAP and DPC were added, and then 0.91 g of $CH_3CH_2COOH$ (98%, 0.012 mol) was added. The mixture was reacted at 70° C. for 100 hours, and then poured into ice water. The target product in the decanted solution was extracted several times by solvents such as ethyl ether or ethyl acetate. The aqueous phase was discarded and the organic phase was combined. The organic solvent was removed after dried over anhydrous magnesium sulfate. The resulting crude product was separated by silica gel column, yielding 2.15 g of curcumol propionate with relatively high purity as a colorless oil, i.e. the derivative of formula (III) wherein $R^1$ is $CH_3CH_2CO$, yield: 82.1%, HPLC: 98.8%.

Finnigan MAT8430 Mass spectrometric analysis showed that the molecular weight of the product was 292.

The spectrum showed 18 carbon signals, 28 proton signals, using BrukerACF-300 nuclear magnetic resonance spectrometer and using $CDCl_3$ as a solvent.

(3) 2.48 g (95%, 0.01 mol) of curcumol was dissolved in 30 mL of acetic anhydride and heated under reflux for several hours. Then the reaction mixture was poured into ice water and the excessive acetic anhydride was neutralized with aq. NaOH solution. The pH of aqueous solution was adjusted to 7-8. The target product in the decanted solution was extracted several times by solvents such as ethyl ether or ethyl acetate. The aqueous phase was discarded and the organic phase was combined. The organic solvent was removed after dried over anhydrous magnesium sulfate. The resulting crude product was separated by silica gel column, yielding 1.8 g of curcumol propionate with relative high purity as a light yellow oil, i.e. Compound No. 1, yield 64%. HPLC: 99.1%.

(4) 2.48 g (95%, 0.01 mol) of curcumol was dissolved in 50 mL of chloroform, and 1.9 g (97%, 0.012 mol) of p-methyl benzoyl chloride and 5 mL of pyridine were added. The mixture was heated under reflux for several hours and poured into ice water. The target product in the decanted solution was extracted several times by solvents such as ethyl ether or ethyl acetate. The aqueous phase was discarded and the organic phase was combined. The organic solvent was removed after dried over anhydrous magnesium sulfate. The resulting crude product was separated by silica gel column, yielding 2.3 g of curcumol p-methyl benzoate with relative high purity as a white oil, i.e. the derivative of formula (I) wherein $R^1$ is $CH_3ArCO$ (as shown in the following formula XV), yield 64.7%. HPLC: 99.5%.

Finnigan MAT8430 Mass spectrometric analysis showed that the molecular weight of the product was 354.

The spectrum showed 23 carbon signals, 30 proton signals, using BrukerACF-300 nuclear magnetic resonance spectrometer and using $CDCl_3$ as a solvent.

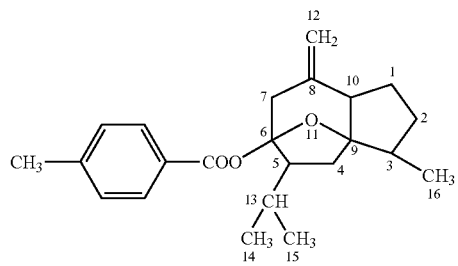

XV (5) 1 g of curcumol was dissolved in 30 mL of DMF, and 2 mL of thionyl chloride was dissolved in 10 mL of DMF. The thionyl chloride solution was added dropwise to the curcumol solution. The temperature of the reaction solution was kept at 20-25° C. and reacted for 3 hours. Then the reaction mixture was poured into 100 mL of water and hydrolyzed for 2 hours. The mixture was extracted with 60 mL of ethyl ether, yielding oily curcumol sulfate, which was separated by silica gel column to afford 0.87 g of product, HPLC: 98.5%. The product was dissolved in 5 mL of methanol and adjusted with 1N NaOH solution to pH 8. The resulting mixture was evaporated to dryness and the residue was treated with ethyl acetate, yielding sodium curcumol sulfate salt as a brown powder, which was soluble in water, i.e. the derivarive of formula (III) wherein $R^1$ is $HO_3S$ or $NaO_3S$ (Compound No. 20 or Compound No. 21). The $NaO_3S$ derivative was detected:

Nuclear magnetic resonance spectrum showed 15 carbon signals, 23 proton signals, using $CDCl_3$ as a solvent.

Mass spectrometric analysis showed that the molecular weight of the product was 354.

Preparation Example 2

Preparing Alkylated Curcumol (the Hydroxy Group at $^6C$)

To a 100 mL of three-necked flask equipped with a stirrer, a thermometer of 0-50° C. and a 25 mL of constant pressure dropping funnel were added 2.45 g (0.01 mol, 96%) of curcumol, 60 mL of isopropyl ether and 5 mL of dichlormethane. After complete dissolvation under stirring, a small amount of anhydrous magnesium sulfate was added and stirred for 3 hours. Magnesium sulfate was removed by filtration. 1.55 g (0.012 mol) of dimethyl sulfate was dissolved in the constant pressure dropping funnel containing 10 mL of dried isopropyl ether. The stirring was initiated and the temperature of the solution was kept at 35° C. The dimethyl sulfate solution was added dropwise slowly. After the completion of addition, NaOH solution (0.025 mol) was added dropwise and continued to stir for more than 12 hours. Then the reaction mixture was poured into 60 g of ice water and extracted with 70 mL of ethyl ether three times (30, 30, 10 mL). The combined ethyl ether was washed with water until it was neutral. Then the ethyl ether solution was dried over anhydrous magnesium sulfate. The magnesium sulfate was removed by filtration. The ethyl ether was removed under vacuum at room temperature to afford a puce solid, which was purified with 1: 50-100 folds of silica gel (200-300 mesh) and eluted with petroleum ether: ethyl acetate=95:5, yielding 1.9 g (content: 99.2% (HPLC)) of the curcumol derivative with the hydroxy group at $^6C$ being methylated, (i.e. the compound of formula III wherein $R^1$ is $CH_3$—, and $R^2$ is H), yield: 76%, MP: 71-73° C.

Element Analysis found: C, 76.935%; H, 10.296%.

Molecular formula ($C_{16}H_{26}O_2$) calculated: C, 76.752%; H, 10.467%.

Nuclear magnetic resonance spectrum showed 16 carbon signals, 26 proton signals, using $CDCl_3$ as a solvent.

Mass spectrometric analysis showed that the molecular weight of the product was 250.

This indicated that the resulting product was our tardet product, i.e. the curcumol methyl ether derivative with $^6C$ being converted into methoxy. The formula was as follows:

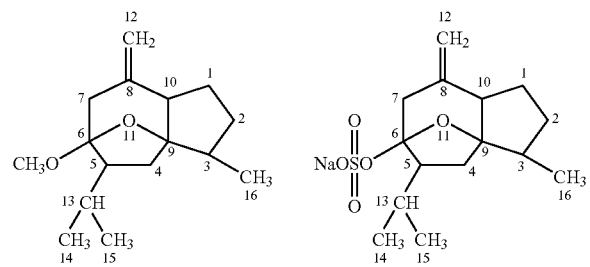

curcumol methyl ether derivative    sodium curcumol sulfate

Preparation Example 3

Preparing the Adduct Obtained from Curcumol and Halogen (1) 2.45 g (0.01 mol, 96%) of curcumol was dissolved in 45 mL of methanol. The mixture was dried over a small amount of anhydrous magnesium sulfate, and then the magnesium sulfate was removed by filtration. The reactant was kept at 5-10° C. and 0.61 mL of (3.15 g/mL, 0.012 mol) of dry liquid bromine was added dropwise to the solution of curcumol in methanol slowly under good stirring. After the addition of bromine, the reaction was continued to stir for 5-30 minutes until the solution was colorless. The methanol was removed under vacuum, yielding crude curcumol bromide, which was directly used in Example 6, or this light yellow crude product may be separated by silica gel column to afford 2.81 g of relatively pure target product as a nearly colorless thick oil, yield: 71%, HPLC: 99.2%, i.e. the curcumol dibromide of formula II wherein $R^1$ is H, $R^2$, $R^3$ are both bromine atom (Compound No. 30).

Element Analysis found: C, 45.630%; H, 6.028%.

Molecular formula ($C_{15}H_{24}O_2Br_2$) calculated: C, 45.477%; H, 6.107%.

Nuclear magnetic resonance spectrum showed 15 carbon signals, 24 proton signals, using $CDCl_3$ as a solvent.

Mass spectrometric analysis showed that the molecular weight of the product was 396.

This indicated that the resulting product was our target product, Compound No. 30.

(2) 2 g (0.005 mol) of dibromide from step (1) was dissolved in 40 mL of anhydrous methanol. A small amount of anhydrous magnesium sulfate was added and stirred. The magnesium sulfate was removed by filtration, and then a dried solution of 0.21 g (95%, 0.005 mol) NaOH in methanol was added. The mixture was stranded for more than 12 hours at room temperature. Then the dark reaction mixture was poured into water and extracted with ethyl ether several times. The ethyl ether layer was washed with water until the pH of the wash solution was about 7. After the ethyl ether was dried over anhydrous magnesium sulfate, the solvent was removed under vacuum to afford a dark and thick substance. After separating by silica gel column, a curcumol derivative with removal of a hydrogen bromide between the carbon carbon atoms of 8- and 12-position and thus formation of a double bond was obtained. 0.83 g of curcumol monobromide derivative (Compound No. 34) was obtained, yield: 53%, HPLC: 98.2%, a light yellow oil (Formula XI, wherein $R^1$ is H, $R^2$ is Br).

Element Analysis found: C, 57.214%; H, 7.650%.

Molecular formula ($C_{15}H_{24}O_2Br$) calculated: C, 56.967%; H, 7.649%.

Nuclear magnetic resonance spectrum showed 15 carbon signals, 24 proton signals, using $CDCl_3$ as a solvent.

Mass spectrometric analysis showed that the molecular weight of the product was 316.

This confirmed that the obtained product was Compound No. 34.

Preparation Example 4

Preparing the Adduct Obtained from Curcumol and Halogen Acid 2.45 g (0.01 mol, 96%) of curcumol was dissolved in 45 mL of methanol. A small amount of anhydrous magnesium sulfate was added and stirred, and then the magnesium sulfate was removed by filtration. The reactant was kept at 5-10° C. and an excess of dry hydrogen bromide (the mole of hydrogen bromide is 1.2 fold of the mole of curcumol) was slowly introduced to the solution of curcumol in methanol slowly under good stirring. After this addition, the reaction mixture was continued to stir about 1 hours, yielding puce crude curcumol monobromide, which was separated by silica gel column to afford relatively pure target product curcumol monobromide, i.e., the curcumol monohalide of formula (II), wherein $R^3$ is bromine atom and $R^2$ is H (Compound No. 34).

Element Analysis found: C, 57.965%; H, 7.582%.

Molecular formula ($C_{15}H_{25}O_2Br$) calculated: C, 56.786%; H, 7.943%.

Nuclear magnetic resonance spectrum showed 15 carbon signals, 25 proton signals, using $CDCl_3$ as a solvent.

Mass spectrometric analysis showed that the molecular weight of the product was 317.

This indicated that the obtained product was our target compound.

The bromide or fluoride obtained above was dissolved in anhydrous methanol, and to it was added fluoride (such as $NH_4F$, NaF) and reacted at room temperature, yielding the corresponding curcumol fluoride.

Preparation Example 5

Preparing of Hydrogenated Curcumol (1) 2.45 g (0.01 mol, 96%) of curcumol was dissolved in 45 mL of methanol. A small amount of anhydrous magnesium sulfate was added and stirred, and then the magnesium sulfate was removed by filtration. A small amount of catalyst for the hydrogenation (such as Pd/C and the like) was added, and hydrogen was introduced under room temperature and normal pressure with vigorous stirring. The hydrogenation reaction was kept for more than 24 hours. After the completion of the hydrogenation reaction, Pd/C was recovered by filtration. The solvent methanol of the filtrate was removed under vacuum at room temperature to afford a light yellow oil. After purified by silica gel column, 1.9 g of nearly colorless powder was obtained with the double bond at position 8-12 of curcumol addition by hydrogen (curcumol dihydrogen derivative), HPLC: 98.1%, Melting point: 75-77° C., i.e., the curcumol dihydrogen derivative of formula (II), wherein $R^1$ is H, $R^2$, $R^3$ are both H (Compound No. 33).

Element Analysis found: C, 75.832%; H, 10.856%.

Molecular formula ($C_{15}H_{26}O_2$) calculated: C, 75.581%; H, 10.994%.

Nuclear magnetic resonance spectrum showed 15 carbon signals, 26 proton signals, using $CDCl_3$ as a solvent.

Mass spectrometric analysis showed that the molecular weight of the product was 238. This indicated that the obtained product was our target compound.

(2) 1 g (96%, 0.004 mol) of curcumol was dissolved in 50 mL of anhydrous ethyl ether. To the reaction mixture was added dropwise $LiAlH_4$ (about 0.005 mol) at room temperature. After addition, the mixture was continued to stir for 3 hours under dry condition. The ethyl ether was removed under vacuum to afford a light yellow powder. After purified by column, 0.58 g of white powder was obtained, yield: 61%, HPLC: 98%, Melting point: 78-80° C., i.e. curcumol derivative of formula (II), wherein $R^2$, $R^3$ are both H (Compound No. 33) was obtained.

Element Analysis found: C, 75.832%; H, 10.856%.

Molecular formula ($C_{15}H_{26}O_2$) calculated: C, 75.581%; H, 10.994%.

Nuclear magnetic resonance spectrum showed 15 carbon signals, 26 proton signals, using $CDCl_3$ as a solvent.

Mass spectrometric analysis showed that the molecular weight of the product was 238.

This indicated that the obtained product was our target compound, dihydro curcumol derivative (Compound No. 33).

Preparation Example 6

Preparation of Halogen Atom Replacement Product of Curcumol Halide (1) 6.0 g (66%, 0.01 mol) curcumolbromide prepared in Preparation Example 3(1) was dissolved in 80 mL of acetonitrile. A small amount of anhydrous magnesium sulfate was added and stirred for 3 hours, and then the magnesium sulfate was removed by filtration. 2.6 g (98%, 0.033 mol) of dried n-butyl amine was added and stranded for more than 24 hours at room temperature. The solvent was removed under vacuum at room temperature. The light yellow mixture was dissolved in 50 mL of water and 60 mL of ethyl acetate and was placed in a pear shape separatory funnel. The solution was adjusted to pH more than 9 with alkaline solution such as ammonia and was shaken thoroughly. The aqueous layer was extracted with 10 mL of ethyl acetate once. The ethyl acetate layer was combined and washed with water (20 mL×4). 40 mL of water was added, and the solution was adjusted to pH less than 7, preferably pH 3 with hydrochloric acid and shaken thoroughly. The ethyl acetate was discarded. The acidic aqueous solution was washed with 20 mL of ethyl ether (three times), and the ethyl ether was discarded. 60 mL of new ethyl acetate was mixed with aqueous phase, and the mixture was adjusted to pH>9 and shaken thoroughly. The aqueous layer was extracted with 10 mL of ethyl acetate once. The ethyl acetate was combined and washed with water (20 mL×4), and then dried over anhydrous magnesium sulfate. The ethyl acetate was removed under vacuum at room temperature to afford 3.2 g of light colored crystal. After separated by column, 2.2 g of the corresponding curcumol n-butyl amine compound was obtained, (or recrystallized with acetone) to obtain a colorless granule crystal, yield: 71.66%, HPLC: 99.8%. Melting point: 104-106° C., i.e., the derivative of formula (III), wherein $R^1$ is H, $R^2$ is $CH_3CH_2CH_2CH_2NH$ (Compound No. 13).

Element Analysis found: C, 74.402%; H, 10.650%; N, 4.62%.

Molecular formula ($C_{19}H_{33}O_2N$) calculated: C, 74.267%; H, 10.749%; N, 4.56%.

Nuclear magnetic resonance spectrum showed 19 carbon signals, 33 proton signals, using $CDCl_3$ as a solvent.

Mass spectrometric analysis showed that the molecular weight of the product was 307.

This indicated that the obtained product was Compound No. 13.

The curcumol n-butyl amine derivative prepared above was dissolved in acetone. Concentrated hydrochloric acid was added dropwise (or HCl gas was introduced) at 20-30° C. with stirring. The solution was made pH 6-7. White curcumol n-butyl amine hydrochloride solid precipitated out of the solution immediately. The solid was filted, washed and dried to afford curcumol n-butyl amine derivative hydrochloride crystai of high purity (Compound No. 14). HPLC: 99.95%, Melting point: 127-129° C.

(2) 6.0 g (66%, 0.01 mol) curcumol bromide prepared in Preparation Example 3(1) was dissolved in 80 mL of acetonitrile. A small amount of anhydrous magnesium sulfate was added and stirred for 3 hours, and then the magnesium sulfate was removed by filtration. 2.6 g (98%, 0.033 mol) of dried t-butyl amine was added and stranded for more than 24 hours at room temperature. The solvent was removed under vacuum at room temperature. The light yellow mixture was dissolved in 50 mL of water and 60 mL of ethyl acetate and was placed in a pear shape separatory funnel. The solution was adjusted to pH more than 9 with alkaline solution such as ammonia and was shaken thoroughly. The aqueous layer was extracted with 10 mL of ethyl acetate once. The ethyl acetate layer was combined and washed with water (20 mL×4). 40 mL of water was added, and the solution was adjusted to pH<7, preferably pH 3 with hydrochloric acid and shaken thoroughly. The ethyl acetate was discarded. The acidic aqueous solution was washed with 20 mL of ethyl ether (three times), and the ethyl ether was discarded. 60 mL of new ethyl acetate was mixed with aqueous phase, and the mixture was adjusted to pH>9 and shaken thoroughly. The aqueous layer was extracted with 10 mL of ethyl acetate once. The ethyl acetate was combined and washed with water (20 mL×4), and then dried over anhydrous magnesium sulfate. The ethyl acetate was removed under vacuum at room temperature to afford 3.0 g of light colored crystal. After separated by silica gel column, 2.0 g of the corresponding curcumol t-butyl amine compound was obtained as a colorless solid (Compound No. 15), yield: 65.4%, HPLC: 98.8%.

Melting point: 79-80° C. i.e. the derivative of formula (III) wherein $R^1$ is H, $R^2$ is $(CH_3)_3CNH$—.

Nuclear magnetic resonance spectrum showed 19 carbon signals, 33 proton signals, using $CDCl_3$ as a solvent.

Mass spectrometric analysis showed that the molecular weight of the product was 307.

This indicated that the obtained products were our target compounds with the following formula:

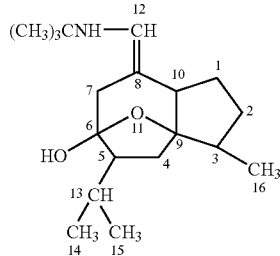

curcumol t-butyl amine derivative

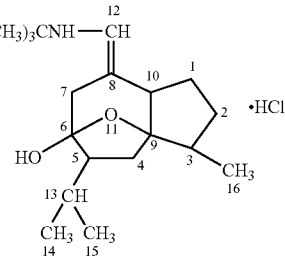

curcumol t-butyl amine derivative hydrochloride

The curcumol t-butyl amine derivative prepared above was dissolved in acetone. Concentrated hydrochloric acid was added dropwise (or HCl gas was introduced) at 20-30° C. with stirring. The solution was made pH 6-7. White curcumol t-butyl amine hydrochloride powder solid precipitated out when acetone was evaporated (Compound No. 16). The structure formula is shown above. HPLC: 99.95%, Melting point: 115-116° C.

(3) 6.0 g (66%, 0.01 mol) curcumol bromide prepared in Preparation Example 3(1) was dissolved in 80 mL of acetonitrile. A small amount of anhydrous magnesium sulfate was added and stirred for 3 hours, and then the magnesium sulfate was removed by filtration. 3.34 g (98%, 0.03 mol) of p-hydroxy aniline was added and stranded for more than 24 hours at room temperature. The solvent was removed under vacuum at room temperature. The dark mixture was dissolved in 50 mL of water and 100 mL of ethyl acetate and was placed in a pear shape separatory funnel. The solution was adjusted to pH>9 with alkaline solution such as ammonia and was shaken thoroughly. The aqueous layer was extracted with 10 mL of ethyl acetate once. The ethyl acetate layer was combined and washed with water of pH 8-9 (20 mL×4). Then 40 mL of water was added, and the solution was adjusted to pH<7, preferably pH 3 with hydrochloric acid and shaken thoroughly. The ethyl acetate was discarded. The acidic aqueous solution was washed with 20 mL of ethyl ether (three times), and the ethyl ether was discarded. 100 mL of new ethyl acetate was mixed with aqueous phase, and the mixture was adjusted to pH>8-9 and shaken thoroughly. The aqueous layer was extracted with 10 mL of ethyl acetate once. The ethyl acetate was combined and washed with water (20 mL×4), and then dried over anhydrous magnesium sulfate. The ethyl acetate was removed under vacuum at room temperature to afford 3.8 g of light yellow solid. After separated by silica gel column, 2.30 g of the corresponding curcumol p-hydroxy aniline compound was obtained, (or after recrystallization) to obtain a white crystal, yield: 67.1%, HPLC: 99.2%, i.e. the derivative of formula (III) wherein $R^1$ is H, $R^2$ is HOArNH—. (Compound No. 5). The structure formula was shown below:

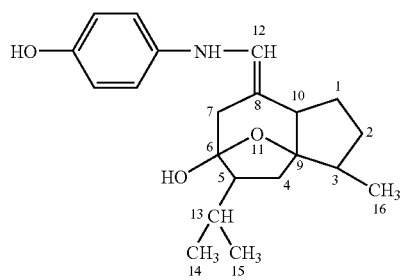

p-hydroxy aniline derivative of curcumol

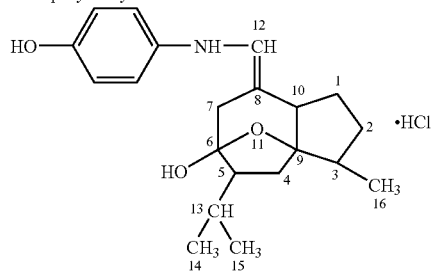

p-hydroxy aniline hydrochloride of curcumol

The p-hydroxy aniline derivative of curcumol prepared above was dissolved in acetone. Concentrated hydrochloric acid was added dropwise (or HCl gas was introduced) at 40-50° C. with stirring. The solution was made pH 5-6. A light yellow curcumol amine hydrochloride crystal precipitated out after being stranded, i.e. off-white curcumol p-hydroxy aniline hydrochloride crystal of high purity was obtained (Compound No. 6, the structure formula is shown above). HPLC: 99.89%, Melting point: 147.5-149.5° C. The hydrochloride was detected:

Nuclear magnetic resonance spectrum showed 21 carbon signals, 30 proton signals, using $CDCl_3$ as a solvent.

Mass spectrometric analysis showed that the molecular weight of the product was 379.5.

This indicated that the obtained product was our target compound.

(4) 6.0 g (66%, 0.01 mol) curcumol bromide prepared in Preparation Example 3(1) was dissolved in 80 mL of acetonitrile. A small amount of anhydrous magnesium sulfate was added and stirred for 3 hours, and then the magnesium sulfate was removed by filtration. 2.90 g (98%, 0.031 mol) of anhydrous piperazine was added and stranded for more than 24 hours at room temperature. The solvent was removed under vacuum at room temperature. The light yellow mixture was dissolved in 50 mL of water and 100 mL of ethyl acetate and was placed in a pear shape separatory funnel. The solution was adjusted to pH>9 with alkaline solution such as ammonia and was shaken thoroughly. The aqueous layer was extracted with 10 mL of ethyl acetate once. The ethyl acetate was combined and washed with water of pH 8-9 (20 mL×4). Then 40 mL of water was added, and the solution was adjusted to pH 3 with hydrochloric acid. The ethyl acetate was discarded. The acidic aqueous solution was washed with mL of ethyl ether (three times), and the ethyl ether was discarded. 100 mL of new ethyl acetate was mixed with acidic aqueous phase, and the mixture was adjusted to pH>9 and shaken thoroughly. The aqueous layer was further extracted with 10 mL of ethyl acetate once. The ethyl acetate was combined and washed with water (20 mL×4), and then dried over anhydrous magnesium sulfate. The ethyl acetate was removed under vacuum at room temperature to afford 3.1 g of white solid. After separated by silica gel column, 2.3 g of the corresponding curcumol piperazine derivative was obtained, (or after recrystallization) to obtain a white crystal, yield: 71.8%, HPLC: 99.2%, Melting point: 128-130° C., i.e. the derivative of formula (III) wherein $R^1$ is H, $R^2$ is

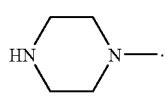

(Compound No. 7)

Nuclear magnetic resonance spectrum showed 19 carbon signals, 32 proton signals, using $CDCl_3$ as a solvent.

Mass spectrometric analysis showed that the molecular weight of the product was 320.

This confirmed that the obtained product was Compound No. 7.

The above-prepared piperazine derivative of curcumol was dissolved in acetone. Concentrated hydrochloric acid was added dropwise (or HCl gas was introduced) at 40-50° C. with stirring. The solution was made pH 5-6. A white curcumol amine hydrochloride crystal precipitated out after stranded. The crystal was decolored by activated carbon in water and recrystallized, yielding off-white curcumol piperazine hydrochloride crystal of high purity (Compound No. 8). HPLC: 99.89%, Melting point: 150-152° C.

Similarly, using the above method, ethyl amine was reacted with curcumol dihalide, yielding the curcumol ethyl amine derivative as a beige powder crystal, i.e. the derivative of formula (III) wherein $R^1$ is H, $R^2$ is $CH_3CH_2NH$, Melting point: 92-94° C., yield: 76%.

(5) 6.0 g (66%, 0.01 mol) curcumol bromide prepared in Preparation Example 3(1) was dissolved in 40 mL of the solution of methanol in water (methanol: water=90:10). 1.5 g of 30% NaOH solution was added dropwise over 10 hours at room temperature. The reaction mixture was stranded for more than 24 hours. The pH of solution was adjusted to neutral. Then 40 mL of water was added and the mixture was extracted with 50 mL of ethyl acetate several times. The ethyl ether was combined and washed with water several times, and then dried over a small amount of anhydrous sodium sulfate. The solvent was removed under vacuum to afford 1.4 g of puce and thick oil. After separated by silica gel column, 0.87 g of curcumol dihydroxy derivative was obtained as a light colored crystal, yield; 65%, Melting point: 163-165° C., HPLC: 98.3%, i.e. the compound of formula (II) wherein $R^3$, $R^2$ are both OH (Compound No. 32, curcumol dihydroxy compound).

Element Analysis found: C, 66.873%; H, 9.458%.

Molecular formula ($C_{15}H_{26}O_4$) calculated: C, 66.636%; H, 9.693%.

Nuclear magnetic resonance spectrum showed 15 carbon signals, 26 proton signals, using $CDCl_3$ as a solvent.

Mass spectrometric analysis showed that the molecular weight of the product was 270.

This indicated that obtained the products were our target compounds with the following formula:

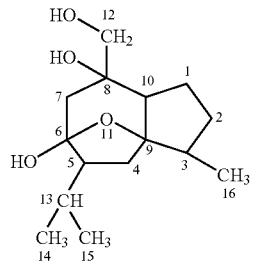

curcumol dihydroxy compound

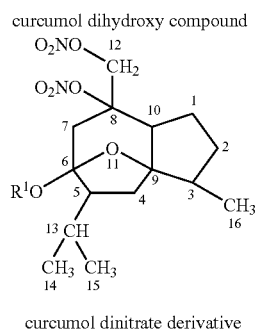

curcumol dinitrate derivative (6) 6.0 g (66%, 0.01 mol) curcumol bromide prepared in Preparation Example 3(1) was dissolved in 60 mL of methanol. To this solution was added dropwise 10 mL of aqueous solution containing 3.6 g (99%, 0.02 mol) silver nitrate and stranded overnight. A large amount of white flocculent precipitate separated out. 60 mL of water and ether (1:1) was added and extracted twice. Silver bromide was recovered from aqueous phase, and ethyl ether phase was washed with 40 mL of water twice, and dried over anhydrous sodium sulfate. The solvent was removed under vacuum to afford curcumol dinitrate derivative, i.e. the derivative of formula (II), wherein $R^3$, $R^2$ are replaced by $NO_3$. The structure formula was shown above (Compound No. 31, curcumol dinitrate derivative).

Preparation Example 7

Preparing Curcumol Derivative with Double Bond being Oxidized (1) 2.45 g (0.01 mol. 96%) of curcumol was dissolved in 40 mL of acetonitrile. The resulting mixture was treated with an aqueous solution containing 1.6 g potassium permanganate (98%, 0.01 mol) and stranded at room temperature until the amaranth of the solution was completely faded. Then the acetonitrile was removed under vacuum. The residue was extracted with 1:1 ethyl acetate-water (100 mL). The aqueous phase was discarded and the ethyl acetate phase was washed with water twice, and then dried over anhydrous sodium sulfate. A dark solid was obtained after the solvent was removed. After separated by silica gel column, 2.1 g of off-white crystal was obtained, yield, 77.7%, Melting point: 163-165° C., HPLC: 98.8%, i.e. the compound of formula (II) wherein $R^1$ is H, $R^2$ and $R^3$ are OH (curcumol dihydroxy compound), whose solubility in water is very big.

Element Analysis found: C, 66.873%; H, 9.458%.

Molecular formula ($C_{15}H_{26}O_4$) calculated: C, 66.636%; H, 9.693%.

Nuclear magnetic resonance spectrum showed 15 carbon signals, 26 proton signals, using $CDCl_3$ as a solvent.

Mass spectrometric analysis showed that the molecular weight of the product was 270.

This indicated that the obtained product was our target compound.

The resulting curcumol dihydroxy derivative was alkylated or esterified to afford the curcumol derivative of formula (II) wherein $R^5$, $R^6$ are both $R^1O$, $R^1$ was defined as above.

(2) 2.45 g (0.01 mol, 96%) of curcumol was dissolved in 40 mL of acetic acid, and to it was added an aqueous solution dissolved with 4 g potassium permanganate. The mixture was heated under reflux for several hours followed by removal of the organic solvent under vacuum. The mixture was extracted with 100 mL of 50% ethyl acetate and water. The ethyl acetate was washed with water several times and dried over anhydrous sodium sulfate. The solvent wad removed under vacuum to afford a dark solid. After separated by silica gel column, 1.45 g of white curzerenone derivative was obtained, yield: 61%, HPLC: 98%, Melting point: 138-140° C., i.e. Compound No. 31 of formula (III) wherein Z is O.

Element Analysis found: C, 70.865%; H, 9.102%.

Molecular formula ($C_{14}H_{22}O_3$) calculated: C, 70.560%; H, 9.305%.

Nuclear magnetic resonance spectrum showed 14 carbon signals, 22 proton signals, using $CDCl_3$ as a solvent.

Mass spectrometric analysis showed that the molecular weight of the product was 238.

This indicated that the obtained product was our target compound with the following formula.

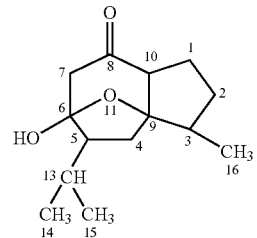

Preparation Example 8

Preparing the Epoxy Derivative of Curcumol 1 g curcumol (96%, 0.004 mol) was dissolved in 100 mL of chloroform. To it was added 2 g m-chloro-benzoyl hydroperoxide (98%, 0.011 mol) at room temperature, and reacted at 15-20° C. for 8 hours. The mixture was washed with 5% sodium hydroxide solution several times and further washed with water to be neutral, and then dried over anhydrous sodium sulfate. The solvent was removed under vacuum. The residue was purified by silica gel column, to afford the epoxy derivative of curcumol of formula (III)(Compound No. 48), wherein, Z is

yielding 0.504 g white powder, yield: 50%, HPLC: 98.5%. Melting point: 130-132° C.

Element Analysis found: C, 70.865%; H, 9.102%.

Molecular formula ($C_{15}H_{24}O_3$) calculated: C, 71.035%; H, 9.046%.

Nuclear magnetic resonance spectrum showed 15 carbon signals, 24 proton signals, using $CDCl_3$ as a solvent.

Mass spectrometric analysis showed that the molecular weight of the product was 252.

This indicated that the obtained product was our target compound with the following formula.

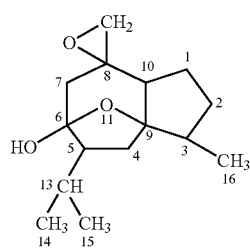

The oxygen ring of the above compound was opened in mild acidic solution to afford the compound of formula (II) wherein $R^2$ is OH, $R^3$ is H. The esterification (or alkylation) of the ring-opening compound (Method 1: the hydroxy group at $^6C$ of curcumol was esterified; Method 2: the hydroxy group at 6C of curcumol was alkylated) afforded the compound of formula (II) wherein $R^3$ is H, $R^2$ is $OR^1$ (wherein $R^1$ was defined as above).

TEST EXAMPLES

Example 1

Measurement of In Vitro Inhibition Rate to Tumor Cells

1. Experimental Compounds

Fifty compounds in total: new compounds 1-49, and Curcumol E.

2. Materials (1) MTT MTT was dissolved in 0.01 mol/L phosphate buffered saline (PBS) at a final concentration of 4 mg/ml. The resulting solution was sterilized by filtration, and stored at 4° C.

(2) Preparation of MTT lysis solution 80 g of sodium dodecylsulphate was dissolved in 200 ml of DMF with water bath. 200 ml of distilled water was added. The pH value was adjusted to 4.7 with 80% acetic acid and 1N HCl (1:1).

(3) Tumor cell lines

| | |
|---|---|
| U-937 | human histocytic lymphoma |
| A-549 | human lung adenocarcinoma |
| Bel-7402 | human hepatic carcinoma |
| MCF-7 | human mammary adenocarcinoma |
| Hela | human cervical carcinoma |
| HL-60 | human promyelocytic leukemia |
| SMMC-7721 | human hepatic carcinoma |
| LLC | mouse Lewis lung carcinoma |

3. Methods (1) Single cell suspension was seeded into 96-well plates (×3) (the cells was diluted in the PRMI-1640 minimum medium to $3\times10^4$ cells/ml, 200 ug diluted cells/well). The cells were incubated in an atmosphere of 5% $CO_2$, 100% humidity for 24 hours at 37° C. The experiments were performed in quadruplicate.

(2) The medium was removed. Solutions of the anti-tumor agents (15 compounds) were prepared in a freshly prepared medium at the concentrations indicated in the following Table. 200 μg of the solution was added into each well. Incubation was continued for 48 hours.

(3) 20 μg of 2 mg/ml MTT was added into each well, and incubated for 4 hours.

(4) The medium was removed from the well. The microplates were swiftly turned down to throw-off the medium. 150 μg/well DMSO was added into each well, and vortexed at room temperature for 10 minutes.

(5) OD value ($\lambda$=570 nm) was measured with an Enzyme-Linked Detector.

(6) The inhibition rates (IR) of cell growth were respectively calculated based on the following equation:

IR(%)=[1−(average OD of the experimental group/average OD of the control group)]×100%

The results are shown in Table 1. The results indicate that the inhibition rate to Hela cells of all of the compounds exhibited>50%.

The experiments were repeated three times. The results are shown in Tables 1, 2 and 3.

TABLE 1

Results of the screening test for in vitro anti-tumor bioactivity of the compounds Testing parameter: inhibition rate    Concentration: 50 μg/ml

| No. | Results (%) U-937 | Results (%) A-549 | Results (%) Bel-7402 | Results (%) MCF-7 | Results (%) SMMC-7721 | Results (%) HL-60 | Results (%) Hela | Results (%) LLC |
|---|---|---|---|---|---|---|---|---|
| 1 | 45.45 | −9.16 | 32.12 | 45.6 | 23.10 | 23.12 | 51.23 | 1.30 |
| 2 | 71.17 | 4.93 | 23.33 | 45.98 | 12.35 | 12.34 | 70.56 | 2.98 |
| 3 | 91.72 | 7.76 | 14.41 | 32.15 | 8.02 | 3.21 | 69.23 | 6.89 |
| 4 | 52.23 | 10.51 | 43.21 | 49.23 | 5.30 | 42.1 | 73.22 | 1.01 |
| 5 | 93.95 | 90.32 | 80.21 | 90.32 | 85.01 | 91.32 | 94.36 | 3.21 |
| 6 | 90.92 | 91.84 | 81.84 | 91.89 | 86.12 | 93.21 | 95.26 | 88.23 |
| 7 | 93.01 | 65.32 | 55.44 | 88.32 | 3.34 | 90.56 | 90.38 | 85.42 |
| 8 | 90.26 | 60.5 | 54.32 | 89.12 | 4.50 | 91.95 | 91.87 | 12.1 |
| 9 | 87.32 | 65.21 | 45.32 | 56.47 | 1.21 | 86.32 | 82.36 | 4.83 |
| 10 | 85.20 | 62.31 | 44.68 | 56.32 | 7.79 | 87.20 | 87.98 | 4.18 |
| 11 | 85.3 | 60.12 | 43.25 | 58.39 | 33.88 | 70.23 | 91.64 | 11.77 |
| 12 | 80.3 | 60.32 | 43.08 | 54.89 | 32.03 | 60.21 | 83.78 | −10.89 |

TABLE 1-continued

Results of the screening test for in vitro anti-tumor bioactivity of the compounds Testing parameter: inhibition rate — Concentration: 50 µg/ml

| No. | Results (%) U-937 | Results (%) A-549 | Results (%) Bel-7402 | Results (%) MCF-7 | Results (%) SMMC-7721 | Results (%) HL-60 | Results (%) Hela | Results (%) LLC |
|---|---|---|---|---|---|---|---|---|
| 13 | 51.10 | 7.59 | 33.16 | 54.67 | 3.71 | 0.12 | 66.32 | 0.24 |
| 14 | 82.88 | 8.09 | 32.00 | 56.30 | 6.14 | 2.45 | 75.46 | −10.57 |
| 15 | 57.32 | 17.43 | 32.98 | 65.32 | −2.50 | 8.23 | 70.02 | −11.83 |
| 16 | 82.56 | 6.01 | 1.23 | 54.89 | −2.50 | 2.31 | 68.99 | 1.13 |
| 17 | 87.18 | 4.68 | −12.36 | 53.89 | 10.16 | 92.33 | 91.58 | 7.27 |
| 18 | 70.30 | −2.24 | 13.58 | 57.89 | 13.39 | 4.26 | 60.32 | 4.18 |
| 19 | 50.97 | 2.51 | 4.32 | 12.6 | 23.01 | 54.03 | 55.67 | −15.52 |
| 20 | 89.23 | 12.50 | 7.89 | 18.9 | 18.08 | 91.35 | 94.23 | 8.97 |
| 21 | 92.04 | 26.42 | 5.36 | 87.56 | −7.26 | 93.12 | 91.69 | 10.47 |
| 22 | 60.32 | 19.23 | 12.80 | 88.32 | 44.39 | 21.01 | 63.20 | −6.01 |
| 23 | 81.60 | −7.41 | 13.54 | 32.56 | 18.69 | 12.50 | 55.33 | 12.1 |
| 24 | 63.78 | 3.12 | 1.23 | 8.26 | −1.59 | 2.63 | 54.62 | 4.83 |
| 25 | 86.94 | 13.68 | 5.68 | 9.53 | 0.24 | −2.63 | 81.88 | 4.18 |
| 26 | 55.32 | −3.24 | 3.45 | 43.21 | 0.97 | −0.23 | 51.00 | 11.77 |
| 27 | 52.98 | 15.01 | 4.65 | 23.78 | 25.94 | 3.19 | 62.31 | −10.89 |
| 28 | 59.32 | 1.23 | −2.24 | 32.15 | −3.78 | 2.98 | 58.75 | 0.24 |
| 29 | 25.32 | 3.89 | 2.51 | 37.85 | 4.26 | 42.12 | 56.98 | −10.12 |
| 30 | 13.25 | 4.36 | 12.40 | 36.15 | 1.03 | 13.20 | 53.87 | −1.83 |
| 31 | −0.68 | 8.65 | 0.23 | 16.75 | −1.96 | 16.50 | 57.98 | 1.13 |
| 32 | 65.32 | −12.5 | 4.23 | 65.12 | 79.96 | 14.00 | 84.33 | 7.27 |
| 33 | 44.34 | 16.32 | 14.32 | 45.3 | −7.44 | 1.32 | 60.89 | 4.18 |
| 34 | 35.23 | 2.31 | 1.11 | 1.23 | −5.25 | 2.96 | 50.64 | −18.52 |
| 35 | 7.36 | 3.89 | 3.65 | 3.89 | 5.23 | 3.12 | 59.88 | 8.97 |
| 36 | 6.98 | 9.21 | 0.22 | −1.23 | 15.39 | 1.03 | 62.13 | 11.56 |
| 37 | 23.56 | 32.03 | 15.32 | 23.10 | −2.32 | 56.23 | 63.75 | 1.21 |
| 38 | 19.30 | 3.71 | 13.56 | 11.32 | −8.7 | 12.35 | 58.69 | 10.47 |
| 39 | 12.68 | 6.14 | 3.87 | 12.84 | −0.33 | 3.16 | 58.75 | −3.24 |
| 40 | 4.36 | −2.50 | 13.2 | 27.35 | 11.65 | 8.88 | 64.26 | 4.21 |
| 41 | 8.65 | −2.50 | 16.78 | 36.45 | 4.42 | 6.78 | 50.32 | 30.96 |
| 42 | −12.5 | 10.16 | 2.15 | 34.21 | 6.86 | 2.73 | 55.64 | 9.99 |
| 43 | 16.32 | 13.39 | 9.15 | 43.21 | −10.12 | 2.56 | 62.13 | −2.06 |
| 44 | 35.64 | 23.01 | −6.54 | 25.55 | −10.53 | 3.71 | 55.14 | 23.35 |
| 45 | 32.19 | 2.10 | 3.01 | 26.78 | −10.73 | 6.14 | 59.45 | 2.74 |
| 46 | 16.32 | 3.12 | 4.55 | 19.88 | −0.86 | −2.60 | 53.12 | −12.99 |
| 47 | 86.47 | −12.0 | 2.88 | 65.12 | −1.43 | 10.32 | 83.66 | −13.24 |
| 48 | 90.92 | 7.84 | 16.40 | 61.23 | 20.59 | 60.80 | 86.77 | −8.04 |
| 49 | 78.65 | 5.36 | 2.69 | 0.65 | −11.3 | 55.35 | 79.8 | −0.15 |
| E | 28.01 | −0.57 | 4.79 | 55.64 | −11.5 | 1.32 | 86.75 | −3.04 |

TABLE 2

(repeated screening). Results of the screening test for in vitro anti-tumor bioactivity of the compounds Testing parameter: inhibition rate — concentration: 50 µg/ml

| No. | Results (%) U-937 | Results (%) A-549 | Results (%) Bel-7402 | Results (%) MCF-7 | Results (%) SMMC-7721 | Results (%) HL-60 | Results (%) Hela | Results (%) LLC |
|---|---|---|---|---|---|---|---|---|
| 1 | 34.26 | −6.32 | 25.32 | 41.02 | 28.23 | 12.03 | 55.98 | 1.30 |
| 2 | 70.30 | 9.23 | 12.78 | 41.78 | 14.67 | 17.98 | 75.23 | 0.32 |
| 3 | 93.01 | 10.32 | 11.00 | 22.35 | 8.96 | 4.89 | 70.23 | 0.02 |
| 4 | 51.00 | 14.03 | 43.02 | 50.09 | 1.96 | 40.01 | 70.12 | 0.23 |
| 5 | 95.56 | 90.00 | 81.54 | 91.02 | 86.91 | 90.89 | 92.31 | 85.07 |
| 6 | 94.12 | 92.84 | 81.84 | 91.89 | 86.12 | 93.21 | 95.26 | 87.02 |
| 7 | 90.00 | 67.23 | 60.23 | 85.01 | 1.23 | 91.02 | 89.30 | −2.99 |
| 8 | 91.32 | 58.56 | 50.45 | 85.23 | 2.30 | 90.17 | 92.00 | 1.02 |
| 9 | 71.32 | 60.45 | 24.32 | 54.23 | 11.23 | 85.02 | 80.23 | 2.31 |
| 10 | 80.20 | 55.06 | 40.32 | 53.26 | 4.44 | 85.03 | 86.49 | 2.36 |
| 11 | 85.01 | 56.32 | 43.25 | 57.39 | 22.13 | 68.23 | 89.02 | 1.23 |
| 12 | 80.23 | 65.01 | 38.02 | 55.01 | 32.09 | 61.20 | 85.36 | −1.23 |
| 13 | 45.10 | 3.56 | 30.25 | 50.36 | 0.23 | 0.79 | 65.92 | 1.32 |
| 14 | 81.23 | 9.23 | 23.56 | 54.23 | 3.21 | 4.35 | 76.32 | −14.29 |
| 15 | 50.12 | 12.33 | 31.20 | 60.12 | −8.60 | 2.98 | 71.42 | −10.12 |
| 16 | 80.12 | 10.19 | 8.99 | 50.32 | 2.63 | 15.00 | 70.32 | 0.22 |

TABLE 2-continued (repeated screening). Results of the screening test for in vitro anti-tumor bioactivity of the compounds Testing parameter: inhibition rate    concentration: 50 µg/ml

| No. | Results (%) U-937 | Results (%) A-549 | Results (%) Bel-7402 | Results (%) MCF-7 | Results (%) SMMC-7721 | Results (%) HL-60 | Results (%) Hela | Results (%) LLC |
|---|---|---|---|---|---|---|---|---|
| 17 | 85.12 | 5.23 | −10.90 | 50.32 | 0.32 | 90.12 | 92.36 | 2.31 |
| 18 | 69.23 | −0.32 | 11.23 | 54.32 | 0.69 | 7.32 | 65.03 | 0.22 |
| 19 | 42.23 | 3.10 | 8.95 | 0.16 | 12.301 | 55.98 | 50.27 | −16.00 |
| 20 | 90.32 | 13.00 | 5.36 | 16.32 | 1.23 | 92.37 | 90.56 | 9.37 |
| 21 | 89.46 | 20.01 | 2.13 | 85.23 | −1.82 | 90.89 | 90.11 | 1.89 |
| 22 | 50.23 | 12.36 | 0.23 | 85.02 | 40.32 | 21.03 | 61.88 | −6.41 |
| 23 | 83.00 | −1.89 | 10.77 | 23.66 | 4.96 | 13.56 | 60.23 | 13.20 |
| 24 | 52.31 | 0.32 | 4.32 | 35.02 | 12.30 | 0.98 | 50.12 | 1.32 |
| 25 | 82.36 | 14.23 | 2.03 | 8.12 | 8.32 | 1.23 | 75.55 | 1.02 |
| 26 | 54.23 | −3.12 | −3.45 | 41.21 | −0.97 | −0.23 | 56.55 | −11.77 |
| 27 | 50.98 | 5.23 | 2.31 | 14.36 | 20.36 | 5.969 | 60.21 | −10.00 |
| 28 | 51.23 | 2.31 | −0.45 | 19.98 | −1.02 | 4.32 | 60.45 | 1.23 |
| 29 | 12.32 | 1.23 | 3.21 | 30.12 | 5.68 | 42.79 | 50.17 | −1.95 |
| 30 | 13.10 | 4.01 | 9.84 | 30.56 | 4.56 | 4.12 | 56.89 | −4.65 |
| 31 | −12.61 | 4.82 | 8.42 | 14.87 | −4.56 | 2.78 | 55.49 | 1.25 |
| 32 | 67.23 | −12.5 | 4.23 | 65.02 | 82.59 | 13.41 | 80.12 | 7.05 |
| 33 | 43.21 | 14.32 | 14.89 | 39.30 | −1.56 | 7.68 | 59.80 | 3.12 |
| 34 | 23.56 | 9.23 | 0.59 | 4.56 | 0.95 | 3.14 | 51.89 | −11.22 |
| 35 | 0.23 | 2.77 | 6.78 | 9.87 | 4.32 | 3.99 | 64.01 | 8.23 |
| 36 | 5.32 | 1.20 | 0.02 | −2.31 | 14.08 | 2.01 | 65.23 | 11.56 |
| 37 | 32.10 | 34.01 | 12.31 | 5.61 | −8.36 | 50.12 | 62.17 | 0.32 |
| 38 | 13.00 | 0.96 | −9.78 | 10.98 | 1.23 | 11.45 | 60.11 | 1.96 |
| 39 | 10.32 | 321 | 13.56 | 19.73 | −0.98 | 9.58 | 60.99 | −4.57 |
| 40 | 1.02 | −12.37 | 25.43 | 14.38 | −11.36 | 12.96 | 64.12 | 1.95 |
| 41 | −1.02 | −7.89 | 1.23 | 31.28 | 3.12 | 1.86 | 51.23 | 23.65 |
| 42 | −1.03 | 3.12 | 14.36 | 30.12 | 0.79 | 3.14 | 54.03 | 1.79 |
| 43 | 12.30 | 11.24 | −4.98 | 41.94 | −8.98 | 2.00 | 59.66 | −11.23 |
| 44 | 23.56 | 20.33 | 0.23 | 24.11 | −7.89 | 5.37 | 50.01 | 17.565 |
| 45 | 12.32 | 0.32 | 5.02 | 20.73 | −11.23 | 1.23 | 53.12 | 1.32 |
| 46 | 8.65 | 3.78 | 4.65 | 14.98 | −0.45 | −4.56 | 49.56 | −17.56 |
| 47 | 85.39 | −7.85 | 2.35 | 60.49 | −3.25 | 1.96 | 80.79 | −14.00 |
| 48 | 91.23 | 9.48 | 10.23 | 62.38 | 12.11 | 50.23 | 80.79 | −4.32 |
| 49 | 75.23 | 4.23 | 14.02 | 1.56 | −1.78 | 57.89 | 75.65 | 0.12 |
| E | 14.321 | −11.32 | 9.87 | 50.23 | −12.30 | 1.23 | 70.12 | −8.90 |

TABLE 3

(repeated screening). Results of the screening test for in vitro anti-tumor bioactivity of the compounds Testing parameter: inhibition rate    concentration: 50 µg/ml

| No. | Results (%) U-937 | Results (%) A-549 | Results (%) Bel-7402 | Results (%) MCF-7 | Results (%) SMMC-7721 | Results (%) HL-60 | Results (%) Hela | Results (%) LLC |
|---|---|---|---|---|---|---|---|---|
| 5 | 91.03 | 91.23 | 78.97 | 95.53 | 85.01 | 95.14 | 94.55 | 86.54 |
| 6 | 94.09 | 90.12 | 83.56 | 94.13 | 87.12 | 95.55 | 92.33 | 85.02 |
| 7 | 91.23 | 65.29 | 65.23 | 84.12 | 1.23 | 90.23 | 89.12 | −3.66 |
| 8 | 94.36 | 55.89 | 54.89 | 86.23 | 7.98 | 91.08 | 91.47 | 3.12 |
| 20 | 89.98 | 14.32 | 1.23 | 14.23 | 6.56 | 91.72 | 92.47 | 15.32 |
| 21 | 91.45 | 1.23 | 3.12 | 87.58 | −2.93 | 89.79 | 91.67 | 7.58 |
| E | 19.78 | −16.56 | 9.78 | 51.23 | −0.23 | 1.79 | 78.56 | −14.44 |

Example 2

Measurement of In Vitro Anti-Tumor $IC_{50}$ for the Compounds

1. Experimental Compounds

Fifteen compounds in total: 5-14, 17, 20, 21 and E, 5-FU as positive control.

2. Materials (1) MTT: MTT was dissolved in 0.01 mol/L phosphate buffered saline (PBS) at a final concentration of 4 mg/ml. The resulting solution was sterilized by filtration, and stored in the refrigeratory of 4° C.

(2) Preparing MTT lysis solution: 80 g of sodium dodecyl-sulphate was dissolved in 200 ml of DMF with warm water bath. 200 ml of distilled water was added. The pH value was adjusted to 4.7 with 80% acetic acid and 1N HCl (1:1).

(3) Tumor cell lines

| | |
|---|---|
| U-937 | human histocytic lymphoma |
| A-549 | human lung adenocarcinoma |
| Bel-7402 | human hepatic carcinoma |
| MCF-7 | human mammary adenocarcinoma |
| Hela | human cervical carcinoma |
| HL-60 | human promyelocytic leukemia |
| SMMC-7721 | human hepatic carcinoma |
| LLC | mouse Lewis lung carcinoma |

3. Methods (1) Single cell suspension was seeded into 96-well plates (the cells was diluted in the PRMI-1640 minimum medium to $3\times10^4$ cells/ml, 200 μg diluted cells/well). The cells were incubated in an atmosphere of 5% $CO_2$, 100% humidity for 24 hours at 37° C. The experiments were performed in quadruplicate.

(2) The medium was removed. Solutions of the anti-tumor agents (50 compounds) were prepared in a freshly prepared medium at serial concentrations. 200 μg of the solution was added into each well. Incubation was continued for 48 hours.

(3) 20 ug of 2 mg/ml MTT was added into each well, and incubated for 4 hours.

(4) The medium was removed from the well. The microplates were swiftly turned down to throw-off the medium. 150 μg/well of DMSO was added into each well, and vortexed at room temperature for 10 minutes.

(5) OD value ($\lambda$=570 nm) was measured with an Enzyme-Linked Detector.

(6) The graph of cell vitality was plotted, and $IC_{50}$ was calculated.

Results

The results are shown in the following Table 4. These results demonstrate that all of the compounds had a comparable or lower $IC_{50}$ against Hela and U-937 cells relative to Compound E and the positive control(5-FU). It indicates that many new compounds had stronger activities as compared with the parent compound Curcumol, and 5-FU (positive control). Compound 5 and Compound 6 had a strong inhibitory effect to all the eight selected tumor cell lines, indicating they are anti-tumor compounds which have a wide-spectrum. Compound 7 and Compound 8 showed excellent activity not only to Hela and U-937 cell lines, but also to U-937 and HL-60 cell lines.

TABLE 4

Results of screening test for bioactivity of the pharmaceutical compounds ($IC_{50}$)

| | $IC_{50}$ (ug/ml) against tumor cell lines | | | | | | | |
|---|---|---|---|---|---|---|---|---|
| No. | Hela | U-937 | MCF | A-549 | Bel-7402 | HL-60 | LLC | SMMC-7721 |
| 5 | 0.32 | 0.42 | 1.00 | 2.0 | 0.9 | 0.4 | 3.6 | 4.3 |
| 6 | 0.35 | 0.56 | 1.10 | 2.1 | 1.0 | 0.51 | 3.8 | 4.0 |
| 7 | 0.6 | 0.76 | 3.20 | | | 1.61 | | — |
| 8 | 0.59 | 0.81 | 3.28 | | | 1.68 | | — |
| 9 | 1.5 | 1.3 | | | | | | |
| 10 | 1.53 | 2.1 | | | | | | |
| 11 | 2.5 | 0.5 | | | | | | |
| 12 | 2.4 | 0.65 | | | | | | |
| 13 | 1.6 | 0.98 | | | | | | |
| 14 | 1.5 | 0.58 | | | | | | |
| 17 | 1.5 | 0.92 | 4.63 | | | 1.85 | | — |

TABLE 4-continued

Results of screening test for bioactivity of the pharmaceutical compounds ($IC_{50}$)

| | $IC_{50}$ (ug/ml) against tumor cell lines | | | | | | | |
|---|---|---|---|---|---|---|---|---|
| No. | Hela | U-937 | MCF | A-549 | Bel-7402 | HL-60 | LLC | SMMC-7721 |
| 20 | 0.89 | 0.95 | 4.98 | | | 0.45 | | — |
| 21 | 0.75 | 0.89 | 4.99 | — | — | 1.3 | — | — |
| E | 3.23 | — | — | — | — | — | — | — |
| 5-FU | 2.86 | | 1.53 | 0.7 | 0.54 | 0.51 | | |

Example 3

In Vivo Anti-Tumor Activity of the Compounds in Animal Body Activity Against Mouse Grafted Sarcoma S-180

1. The Screened Compounds

Three compounds were selected for the screening test: Compound 6 (Curcumol p-hydroxy aniline hydrochloride), Compound 8 (Curcumol piperazine hydrochloride), and Compound 21 (Curcumol sodium sulfonate).

2. Materials (1) Experimental animals: Kunming mice weighting 18-22 g;

(2) 100 mg/ml solutions of the 3 compounds were prepared, respectively, in water for injection (1% surface surfactant was added into the solution of Compound 6). 5-FU and camptothecine, 30 mg/kg and 1 mg/kg, respectively, were used as positive controls;

(3) 0.9% physiological saline;

(4) Tumor cell lines inoculated: sarcoma S-180.

3. Route of Administration: Intravenous Injection.

4. Methods

The experiments were performed according to "Guideline for New Drugs (Western medicines) in Pre-clinical Stages" issued by Bureau of Drug Policy & Administration of the People's Republic of China, and the relevant methods in "Methodology of Pharmaceutical Experiments", Xu Shuyun et al. ed. 120 male Kunming mice weighting 20-22 kg were allowed to grow 3 days. No abnormality was observed. The mice were routinely inoculated in oxter with mouse sarcoma S-180, and weighted 4 hrs. after inoculation. The mice were randomly divided into 12 groups, 10 mice/group. Group 1 was given 0.3 ml of physiological saline as negative control; Group 2 was given 5-FU as positive control, 0.6 mg/mouse; Group 3 was given hydroxycamptothecine as positive control, 0.02 mg/mouse. Groups 4, 5 and 6 were injected with 10% Compound 6, 0.4 ml/mouse, 0.2 ml/mouse, and 0.1 ml/mouse, respectively. Groups 7, 8 and 9 were injected with 10% Compound 8, 0.4 ml/mouse, 0.2 ml/mouse, and 0.1 ml/mouse, respectively. Groups 10, 11, and 12 were injected with 10% Compound 20, 0.4 ml/mouse, 0.2 ml/mouse, and 0.1 ml/mouse, respectively. The tested compounds were administered on the next day after inoculation, once a day on alternate days, 6 doses totally administered. On the next day after the end dose, the mice were weighed and sacrificed. After the tumor was excised, body weight and tumor weight were recorded. The tumor inhibition rate was calculated based on the following formula: [(average tumor weight of the control groups–average tumor weight of the experimental groups)/average tumor weight of the control groups]×100%. The data was processed statistically. The above experiments were repeated three times.

The results are shown in Table 5. The results indicate that all of the three different concentrations of Compound 6 had a good inhibitory effect against mouse sarcoma S-180; Compound 8 had the inhibitory effect only when the concentration reached 40 mg/kg; while Compound 21 had little inhibitory effect.

Activity Against Mouse Grafted Liver Cancer H22

The experiments were identical with the experiments for activity against mouse grafted sarcoma S-180, except that the cell line inoculated was liver cancer H22. The experiments were repeated three times.

TABLE 5

(the first experiment). Results of activity against mouse grafted sarcoma S-180 (X ± SD, n = 10)

| Group | | Dose (mg/kg) | Average weight(g)- before administration | Average weight (g)- after administration | Tumor weight (g) | Inhibition rate (%) |
|---|---|---|---|---|---|---|
| 1 | Physiological saline | | 20.3 | 22.1 | 2.50 ± 0.32 | |
| 2 | 5-FU | 30 | 19.5 | 22.9 | 0.72 ± 0.23 | 71.2 |
| 3 | Hydroxyca-mptothecine | 1 | 20.6 | 20.8 | 0.87 ± 0.28 | 65.2 |
| 4 | Compound 6 | 40 | 19.9 | 22.0 | 0.62 ± 0.34 | 75.2 |
| 5 | | 20 | 20.3 | 22.9 | 0.79 ± 0.21 | 68.4 |
| 6 | | 10 | 19.6 | 22.3 | 1.1 ± 0.31 | 56 |
| 7 | Compound 8 | 40 | 20.3 | 23.0 | 1.3 ± 0.24 | 48 |
| 8 | | 20 | 19.6 | 21.8 | 2.0 ± 0.40 | 20 |
| 9 | | 10 | 19.9 | 22.5 | 2.1 ± 0.42 | 16 |
| 10 | Compound 21 | 40 | 20.6 | 23.1 | 2.3 ± 0.31 | 8 |
| 11 | | 20 | 19.9 | 22.5 | 2.4 ± 0.43 | 4 |
| 12 | | 10 | 20.1 | 22.6 | 2.6 ± 0.23 | — |

TABLE 5

(the second experiment). Results of activity against mouse grafted sarcoma S-180 (X ± SD, n = 10)

| Group | | Dose (mg/kg) | Average weight(g)- before administration | Average weight(g)- after administration | Tumor weight (g) | Inhibition rate (%) |
|---|---|---|---|---|---|---|
| 1 | Physiological saline | | 20.5 | 22.1 | 2.60 ± 0.32 | |
| 2 | 5-FU | 30 | 19.2 | 21.9 | 0.79 ± 0.33 | 69.6 |
| 3 | Hydroxy-camptothecine | 1 | 20.0 | 20.8 | 0.92 ± 0.38 | 64.6 |
| 4 | Compound 6 | 40 | 19.5 | 22.0 | 0.71 ± 0.44 | 72.7 |
| 5 | | 20 | 20.7 | 21.9 | 0.82 ± 0.32 | 68.8 |
| 6 | | 10 | 20.6 | 22.3 | 1.1 ± 0.31 | 57.7 |
| 7 | Compound 8 | 40 | 20.7 | 23.0 | 1.4 ± 0.37 | 46.1 |
| 8 | | 20 | 20.6 | 21.8 | 2.2 ± 0.29 | 15.4 |
| 9 | | 10 | 21.0 | 23.5 | 2.2 ± 0.31 | 15.4 |
| 10 | Compound21 | 40 | 20.1 | 23.1 | 2.4 ± 0.36 | 7.6 |
| 11 | | 20 | 19.6 | 22.2 | 2.5 ± 0.38 | 3.8 |
| 12 | | 10 | 20.4 | 22.6 | 2.5 ± 0.42 | 3.8 |

The results are shown in Table 6. The results indicate that all of the three different concentrations of Compound 6 had a good inhibitory effect against mouse grafted liver cancer H22; Compound 8 had some inhibitory effect only when the concentration reached 40 mg/kg; while Compound 21 had little inhibitory effect.

TABLE 6

(the first experiment). Results of activity against mouse Liver cancer cell line H22 (X ± SD, n = 10)

| Group | | Dose (mg/kg) | Average weight(g)-before administration | Average weight(g)-after administration | Tumor weight (g) | Inhibition rate (%) |
|---|---|---|---|---|---|---|
| 1 | Physiological saline | | 19.6 | 22.2 | 3.02 ± 0.30 | |
| 2 | 5-FU | 30 | 20.3 | 22.3 | 1.21 ± 0.31 | 60.0 |
| 3 | Hydroxy-camptothecine | 1 | 20.3 | 20.5 | 1.12 ± 0.28 | 63.9 |
| 4 | Compound 6 | 40 | 19.9 | 22.1 | 1.15 ± 0.31 | 61.9 |
| 5 | | 20 | 21.2 | 22.2 | 1.60 ± 0.29 | 47.0 |
| 6 | | 10 | 20.6 | 22.0 | 2.8 ± 0.37 | 7.0 |
| 7 | Compound 8 | 40 | 20.8 | 22.4 | 1.9 ± 0.36 | 37.1 |
| 8 | | 20 | 21.0 | 21.9 | 2.9 ± 0.39 | 4.0 |
| 9 | | 10 | 21.4 | 22.3 | 3.02 ± 0.33 | — |
| 10 | Compound 21 | 40 | 20.5 | 22.1 | 2.9 ± 0.31 | 4.0 |
| 11 | | 20 | 19.2 | 22.0 | 3.03 ± 0.41 | — |
| 12 | | 10 | 20.3 | 22.1 | 3.00 ± 0.29 | — |

TABLE 6

(the second experiment). Results of activity against mouse Liver cancer cell line H22 (X ± SD, n = 10)

| Group | | Dose (mg/kg) | Average weight(g)-before administration | Average weight(g)-after administration | Tumor weight (g) | Inhibition rate (%) |
|---|---|---|---|---|---|---|
| 1 | Physiological saline | | 21.2 | 22.2 | 3.02 ± 0.30 | |
| 2 | 5-FU | 30 | 19.6 | 21.3 | 1.19 ± 0.31 | 60.5 |
| 3 | Hydroxy-camptothecine | 1 | 20.3 | 20.2 | 1.00 ± 0.28 | 66.9 |
| 4 | Compound 6 | 40 | 20.8 | 22.4 | 1.21 ± 0.31 | 60.3 |
| 5 | | 20 | 20.3 | 22.0 | 1.58 ± 0.29 | 47.7 |
| 6 | | 10 | 20.1 | 21.0 | 2.6 ± 0.37 | 13.9 |
| 7 | Compound 8 | 40 | 20.4 | 21.4 | 1.93 ± 0.36 | 36.1 |
| 8 | | 20 | 21.8 | 21.9 | 2.9 ± 0.39 | 4.0 |
| 9 | | 10 | 21.0 | 22.3 | 3.10 ± 0.33 | — |
| 10 | Compound 21 | 40 | 20.5 | 22.1 | 3.0 ± 0.31 | 1.0 |
| 11 | | 20 | 20.3 | 22.0 | 3.02 ± 0.41 | — |
| 12 | | 10 | 19.2 | 22.1 | 3.03 ± 0.29 | — |

TABLE 6

(the third experiment). Results of activity against mouse Liver cancer cell line H22 (X ± SD, n = 10)

| Group | | Dose (mg/kg) | Average weight (g)-before administration | Average weight (g)-after administration | Tumor weight (g) | Inhibition rate (%) |
|---|---|---|---|---|---|---|
| 1 | Physiological saline | | 20.2 | 22.0 | 3.02 ± 0.30 | |
| 2 | 5-FU | 30 | 19.9 | 20.3 | 1.08 ± 0.31 | 64.2 |
| 3 | Hydroxy-camptothecine | 1 | 21.3 | 22.2 | 1.05 ± 0.28 | 65.3 |
| 4 | Compound 6 | 40 | 19.8 | 21.4 | 1.30 ± 0.31 | 56.9 |
| 5 | | 20 | 19.3 | 20.0 | 1.63 ± 0.29 | 46.0 |
| 6 | | 10 | 20.5 | 21.2 | 2.8 ± 0.37 | 7.3 |
| 7 | Compound 8 | 40 | 21.4 | 21.9 | 2.01 ± 0.36 | 33.4 |
| 8 | | 20 | 19.8 | 20.9 | 2.8 ± 0.39 | 7.3 |
| 9 | | 10 | 19.0 | 20.3 | 2.95 ± 0.33 | 2.3 |
| 10 | Compound 21 | 40 | 19.5 | 20.1 | 3.0 ± 0.31 | 1.0 |

TABLE 6-continued (the third experiment). Results of activity against mouse Liver cancer cell line H22 (X ± SD, n = 10)

| Group | Dose (mg/kg) | Average weight (g)- before administration | Average weight (g)- after administration | Tumor weight (g) | Inhibition rate (%) |
|---|---|---|---|---|---|
| 11 | 20 | 19.3 | 21.0 | 3.01 ± 0.41 | — |
| 12 | 10 | 20.2 | 22.1 | 3.02 ± 0.29 | — |

Activity Against Mouse Grafted Uterine Cervix Cancer U14

The experiments were identical with the experiments for activity against mouse grafted sarcoma S-180, except the following:

(1) the tumor cell line inoculated was mouse grafted uterine cervix cancer U14;

(2) all the mice were female.

The experiments were repeated three times.

The results are shown in Table 7. The results indicate that all the three concentrations of Compound 6, Compound 8 and Compound 21 had a good inhibitory effect against mouse grafted uterine cervix cancer U14; when the concentration was above 20 mg/kg, the inhibition rates of all the three compounds against mouse grafted uterine cervix cancer U14 was above 50%; when the concentration was above 40 mg/kg, the inhibition rates of all the three compounds against mouse grafted uterine cervix cancer U14 was above 60%, Compound 6 and Compound 21 even above 70%.

TABLE 7

(the first experiment) Results of the activity against mouse grafted uterine cervix cancer U14 (X ± SD, n = 10)

| Groups | | Dose (mg/kg) | Average weight(g)- before administration | Average weight(g)- after administration | Tumor weight (g) | Inhibition rate (%) |
|---|---|---|---|---|---|---|
| 1 | Physiological saline | | 19.2 | 22.0 | 3.51 ± 0.30 | |
| 2 | 5-FU | 30 | 20.9 | 21.3 | 2.10 ± 0.31 | 40.2 |
| 3 | Hydroxy-camptothecine | 1 | 20.3 | 22.2 | 1.90 ± 0.28 | 45.8 |
| 4 | Compound 6 | 40 | 19.1 | 21.4 | 0.96 ± 0.31 | 72.6 |
| 5 | | 20 | 20.3 | 21.0 | 1.23 ± 0.29 | 65.0 |
| 6 | | 10 | 21.5 | 22.2 | 2.2 ± 0.37 | 37.3 |
| 7 | Compound 8 | 40 | 21.0 | 21.9 | 1.15 ± 0.36 | 67.2 |
| 8 | | 20 | 19.2 | 20.9 | 1.60 ± 0.39 | 54.4 |
| 9 | | 10 | 19.9 | 20.9 | 2.26 ± 0.33 | 35.6 |
| 10 | Compound 21 | 40 | 19.6 | 21.1 | 0.99 ± 0.31 | 71.8 |
| 11 | | 20 | 19.9 | 21.0 | 1.52 ± 0.41 | 56.7 |
| 12 | | 10 | 20.6 | 22.1 | 1.68 ± 0.29 | 52.1 |

TABLE 7

(the second experiment). Results of the activity against mouse grafted uterine cervix cancer U14 (X ± SD, n = 10)

| Groups | | Dose (mg/kg) | Average weight(g)- before administration | Average weight(g)- after administration | Tumor weight (g) | Inhibition rate (%) |
|---|---|---|---|---|---|---|
| 1 | Physiological saline | | 19.8 | 22.6 | 3.40 ± 0.30 | |
| 2 | 5-FU | 30 | 20.0 | 21.3 | 1.95 ± 0.31 | 42.6 |
| 3 | Hydroxy-camptothecine | 1 | 20.6 | 22.3 | 1.82 ± 0.28 | 46.5 |
| 4 | Compound 6 | 40 | 19.9 | 21.6 | 0.90 ± 0.31 | 73.5 |
| 5 | | 20 | 20.3 | 21.6 | 1.20 ± 0.29 | 64.7 |
| 6 | | 10 | 21.5 | 22.0 | 2.3 ± 0.37 | 32.3 |
| 7 | Compound 8 | 40 | 20.3 | 21.2 | 1.20 ± 0.36 | 64.7 |
| 8 | | 20 | 19.6 | 20.9 | 1.51 ± 0.39 | 55.6 |
| 9 | | 10 | 20.9 | 21.9 | 2.08 ± 0.33 | 38.8 |
| 10 | Compound 21 | 40 | 19.8 | 21.0 | 0.89 ± 0.31 | 73.8 |
| 11 | | 20 | 19.9 | 21.1 | 1.46 ± 0.41 | 57.1 |
| 12 | | 10 | 20.6 | 22.5 | 1.59 ± 0.29 | 53.2 |

TABLE 7

(the third experiment). Results of the activity against mouse grafted uterine cervix cancer U14 (X ± SD, n = 10)

| Groups | | Dose (mg/kg) | Average weight (g)- before administration | Average weight (g)- after administration | Tumor weight (g) | Inhibition rate (%) |
|---|---|---|---|---|---|---|
| 1 | Physiological saline | | 19.2 | 22.2 | 3.62 ± 0.30 | |
| 2 | 5-FU | 30 | 20.5 | 21.0 | 2.10 ± 0.31 | 42.0 |
| 3 | Hydroxy-camptothecine | 1 | 20.1 | 21.3 | 1.96 ± 0.28 | 45.6 |
| 4 | Compound 6 | 40 | 20.1 | 21.6 | 1.01 ± 0.31 | 72.1 |
| 5 | | 20 | 19.3 | 21.6 | 1.32 ± 0.29 | 63.5 |
| 6 | | 10 | 20.1 | 22.1 | 2.32 ± 0.37 | 35.9 |
| 7 | Compound 8 | 40 | 20.2 | 21.3 | 1.25 ± 0.36 | 65.5 |
| 8 | | 20 | 19.9 | 21.9 | 1.65 ± 0.39 | 54.4 |
| 9 | | 10 | 20.1 | 21.5 | 2.14 ± 0.33 | 40.1 |
| 10 | Compound 21 | 40 | 19.1 | 20.1 | 0.95 ± 0.31 | 73.7 |
| 11 | | 20 | 19.7 | 21.0 | 1.51 ± 0.41 | 58.3 |
| 12 | | 10 | 20.6 | 22.0 | 1.64 ± 0.29 | 54.7 |

Activity Against Mouse Grafted Lung Cancer Lewis

The experiments were identical with the experiments for activity against mouse grafted sarcoma S-180, except the following:
(1) the tumor cell line inoculated was mouse lung cancer Lewis;
(2) Compound 6, Compound 8 and Compound 21 were not tested for their activity;
(3) the mice were divided into six groups.

The experiments were repeated three times.

The results are shown in Table 8. The results indicate that all the three different concentrations of Compound 6 had some inhibitory effect against mouse lung cancer Lewis, the inhibitory effect being 51.6%, 44.8%, 29.4%, respectively. When the concentration was 40 mg/kg, the inhibition rate was comparable with that of camptothecine (positive control), similar to that of 5-FU.

TABLE 8

Results of the activity against mouse lung cancer Lewis (X ± SD, n = 10)

| Groups | | Dose (mg/kg) | Average weight (g)- before administration | Average weight (g)- after administration | Tumor weight (g) | Inhibition rate (%) |
|---|---|---|---|---|---|---|
| (the first experiment). | | | | | | |
| 1 | Physiological saline | | 20.1 | 23.2 | 2.98 ± 0.30 | |
| 2 | 5-FU | 30 | 19.5 | 21.0 | 1.34 ± 0.31 | 55.0 |
| 3 | Hydioxy-camptothecine | 1 | 19.8 | 21.0 | 1.50 ± 0.28 | 49.7 |
| 4 | Compound 6 | 40 | 20.3 | 21.6 | 1.44 ± 0.31 | 51.7 |
| 5 | | 20 | 19.6 | 21.1 | 1.71 ± 0.29 | 42.6 |
| 6 | | 10 | 20.2 | 22.1 | 2.10 ± 0.37 | 29.5 |
| (the second experiment) | | | | | | |
| 1 | Physiological saline | | 20.3 | 22.6 | 2.41 ± 0.30 | |
| 2 | 5-FU | 30 | 19.8 | 21.5 | 1.10 ± 0.31 | 54.3 |
| 3 | Hydroxy-camptothecine | 1 | 19.1 | 21.0 | 1.20 ± 0.28 | 50.2 |
| 4 | Compound 6 | 40 | 19.3 | 20.6 | 1.19 ± 0.31 | 50.6 |
| 5 | | 20 | 19.2 | 21.8 | 1.34 ± 0.29 | 44.4 |
| 6 | | 10 | 20.9 | 22.9 | 1.80 ± 0.37 | 25.3 |
| (the third experiment) | | | | | | |
| 1 | Physiological saline | | 21.0 | 24.6 | 2.70 ± 0.30 | |
| 2 | 5-FU | 30 | 21.3 | 23.5 | 1.25 ± 0.31 | 53.7 |
| 3 | Hydroxy-camptothecine | 1 | 19.9 | 21.5 | 1.30 ± 0.28 | 51.9 |
| 4 | Compound 6 | 40 | 21.3 | 24.6 | 1.28 ± 0.31 | 52.6 |
| 5 | | 20 | 21.9 | 24.8 | 1.42 ± 0.29 | 47.4 |
| 6 | | 10 | 20.6 | 22.9 | 1.80 ± 0.37 | 33.3 |

Example 4

Screening for In Vitro Activity Against HIV-1 Proteinase (HIV-1 PR)

Principle of the test: HIV-1 proteinase digests the fluorescent-labeled substrate in an optimal reaction condition and system. The activity of the enzyme can be reflected by the fluorescent intensity in the product of the enzyme reaction. Adding a sample into the reaction system can be used for screening the inhibitor of the enzyme.

Materials and Methods:

1. HIV-1 PR: commercially available, stored at −85° C.

2. Treatment of the samples: Before use, sample was dissolved in DMSO at a suitable concentration, then serially diluted (5×) with double distilled water, five serial dilutions per sample.

3. Positive control: indinavir, purchased from GlaxoSmithKline.

4. Methods: The diluted sample was added into the reaction buffer containing the fluorescent-labeled substrate. Then the genetic engineered target enzyme was added, and incubated in the optimal reaction condition. The fluorescent value was measured with a FLUO star Galaxy luminoscope.

Results:

TABLE 9

Results of primary screening of the activity against HIV-1 proteinase.
Inhibition rate and IC$_{50}$ of the compounds at different concentrations

| | No. | | | | | |
|---|---|---|---|---|---|---|
| | 50 (μg/ml) | 10 (μg/ml) | 2.0 (μg/ml) | 0.40 (μg/ml) | 0.08 (μg/ml) | IC50 (μg/ml) |
| Compound 2 | 12.66 | 12.20 | 2.98 | 8.64 | 4.13 | — |
| Compound 3 | 5.55 | 12.06 | 9.64 | 13.48 | 4.98 | — |
| Compound 5 | 1.01 | 11.22 | 10.30 | 9.00 | 4.38 | — |
| Compound 6 | 7.07 | 13.15 | 2.99 | 1.7 | 0.89 | — |
| Compound 7 | 1.43 | 3.51 | 4.31 | 6.32 | 14.06 | — |
| Compound 8 | 1.40 | 0.62 | 5.27 | 2.64 | 9.74 | — |
| Compound 17 | 9.94 | 6.15 | −6.00 | 10.71 | 3.78 | — |
| Compound 20 | 12.68 | 9.46 | 10.57 | 7.44 | 8.76 | — |
| Compound 21 | 5.47 | 10.16 | 5.86 | 14.77 | 8.74 | — |
| Compound 23 | 1.39 | 11.23 | 13.69 | 11.14 | 11.88 | — |
| Compound 24 | −0.63 | 2.57 | 11.62 | 13.48 | 3.32 | — |
| Compound 33 | 9.14 | 1.30 | 10.63 | 11.41 | 13.21 | — |
| Compound 47 | 0.56 | 1.78 | 12.94 | 12.32 | 6.89 | — |
| | 10 nM 92.1 | | | | | |

Note:
"—": The initial concentration of the sample inhibits the activity of HTV-1 proteinase;
"*": The sample itself was fluorescent, which interferes the testing system to yield imprecise results.

The results indicate that none of the compounds at a concentration of 200 ug/ml had activity against the HTV-1 proteinase.

Example 5

Screening for the In Vitro Activity Against the HIV-1 Reverse Transcriptase

Principle of the test: The template to which the HIV-1 reverse transcriptase interacts was covered onto the enzyme-lined template. In the optimal reaction conditions and system, HIV-1 RT will put the substrate comprising Biotin-dUTP onto the reaction template. The activity of the enzyme was measured as the amount of the integrating Biotin-dUTP in the reaction by using streptavidin-labeled horseradish peroxidase. Adding the sample to the reaction system can identify inhibitor of the enzyme.

Materials and Methods:

1. HIV-1 RT: commercially available.

2. Treatment of the samples: Before use, the sample was dissolved in DMSO at a suitable concentration, then serially diluted (5×) with double distilled water, five serial dilutions per sample.

3. Positive control: Nevirapine (NVP), produced by The Third Changzhou Pharmaceutical Company (Changzhou San Chang).

4. Methods: The diluted sample was added into the reaction buffer containing Biotin-dUTP and the genetic engineered target enzyme, and incubated in the optimal reaction conditions. A streptavidin-labeled horseradish peroxidase was added to visual the system, and OD450 was measured.

TABLE 10

Primary screening for the activity against the HIV-1 reverse transcriptase.

| No. | Initial concentration | IC50 |
|---|---|---|
| Compound 2 | 1/150 of the stock solution | * |
| Compound 3 | 1/150 of the stock solution | * |
| Compound 5 | 200 μg/ml | — |
| Compound 6 | 200 μg/ml | — |
| Compound 7 | 200 μg/ml | — |
| Compound 8 | 200 μg/ml | — |
| Compound 17 | 200 μg/ml | — |
| Compound 20 | 200 μg/ml | — |
| Compound 21 | 200 μg/ml | — |
| Compound 23 | 200 μg/ml | — |
| Compound 24 | 200 μg/ml | — |
| Compound 33 | 200 μg/ml | — |
| Compound 47 | 200 μg/ml | — |
| NVP | 10 μg/ml | 0.21 μg/ml |

Note:
"—": The initial concentration of the sample did not inhibit the HIV-1 RT.
*: The initial concentration of the sample inhibited the HIV-1 RT.

The results shows that Compound 2 and Compound 3 in a concentration of 120 ug/ml had 60% inhibition rate of. The new compounds had activity against HIV-1 reverse transcriptase, but the effect was barely good.

Example 6

Screening for the Activity Against HIV-1 Integrase (HIV-1 IN)

Principle of the test: A synthetic oligonucleotide of 30 nt was used as the donor substrate. A synthetic oligonucleotide of 20 nt was used as the target substrate. A 96-well plate was covered by the donor substrate, and a purified HIV-1 integrase was added into each well. ELISA was performed to measure the product of the target DNA chain transfer. A biotin-labeled alkali phosphatase was used to visual the system. OD value was measured by an Enzyme-linked Detector. Add a sample into the reaction system for screening the inhibitor of the enzyme.

Materials and Methods:

1. HIV-1 IN: commercially available.
2. Treatment of the samples: Before use, the sample was dissolved in water or DMSO at a suitable concentration, then serially diluted (5×), four serial dilutions per sample. The stock solutions of two samples were 100-fold diluted with DMSO, then 5-fold diluted, four serial dilutions per sample. Positive control: S-y, provided by Shanghai Organic Chemistry Institute.
3. The donor substrate and target substrate: synthesized by Shanghai Biological Engineering Company (Shanghai Shenggong).
4. Methods: The diluted sample was added into a 96-well plate covered by the donor substrate, and then added into the reaction buffer containing the genetic engineered target enzyme and biotin-target substrate, incubated in the optimal reaction conditions. A biotin-labeled alkali phosphatase was used to visual the system to determine the absorbance at 450 nm (OD450).

Results:

The results shows that Compound 20 had a good inhibitory effect to HIV-1 integrase (HIV-1 IN), $IC_{50}$ being 39.820 ug/ml.

Example 7

Screening for the Activity Against Influenza A Virus and Influenza B Virus

Principle of the test: The MDCK (dog kidney) cells are used as host of virus to measure the inhibition of the cytopathic effect (CPE) induced by the virus.

Materials and Methods:

1. Virus strains: influenza A virus (Jifang 90-15) and influenza B virus (Jifang 97-13) were subcultured in the allantoic cavity of a chick embryo (2003.8), stored at −80° C.
2. Treatment of the samples: The sample was dissolved in DMSO, and then dissolved in medium to reach a suitable initial concentration. The resulting solution was then 3× serially diluted, 8 serial dilution levels per sample.
3. Positive: Virazole (RBV), obtained from Zhejing Kangyu Pharmaceuticals, Co. LTD (Batch No. 960501).
4. Methods: The MDCK cells were seeded into a 96-well plate, and incubated in an atmosphere of 5% $CO_2$ at 37° C. for 24 hours. $10^{-3}$ (60×$TCID_{50}$) of influenza A virus and $10^{-2}$ (30×$TCID_{50}$) of Influenza B virus was added to the MDCK cells, respectively. The medium of the virus was decanted after 2 hrs of incubation at 37° C., and the agents in different dilution levels were added. The control for virus and control for cells were used. After incubation at 37° C. for 36 hrs, CPE were recorded, and the 50% inhibiting concentration ($IC_{50}$) of the samples were calculated.

TABLE 11

Primary screening for activity against the HIV-1 integrase

| No. | Initial concentration (µg/ml) | $IC_{50}$ (µg/ml) | No. | Initial concentration (µg/ml) | $IC_{50}$ (µg/ml) |
| --- | --- | --- | --- | --- | --- |
| Compound 2 | 1/1000 (Stock solution) | 35.681 | Compound 20 | 100 | 39.820 |
| Compound 3 | 1/1000 (Stock solution) | 35.983 | Compound 21 | 100 | — |
| Compound 5 | 100 | — | Compound 23 | 100 | — |
| Compound 6 | 100 | — | Compound 24 | 100 | — |
| Compound 7 | 100 | — | Compound 33 | 100 | — |
| Compound 8 | 100 | — | Compound 47 | 100 | — |
| Compound 17 | 100 | — | | | — |
| S-y | | 0.545 | | | |

Note:
"—": indicates that the initial concentration of the sample had a inhibition rate of less than 50% against HIV-1 IN.

Results:

TABLE 12

Primary screening for the activity against influenza A virus and influenza B virus

| No. | $TC_{50}$ (μg/ml) | influenza A virus $IC_{50}$ (μg/ml) | SI | influenza B virus $IC_{50}$ (μg/ml) | SI |
|---|---|---|---|---|---|
| 25 | >1000 | — | — | — | — |
| 21 | >1000 | 47.72 | 20.96 | — | — |
| E | >1000 | — | — | — | — |
| 6 | 192.45 | — | — | — | — |
| 14 | 143.17 | — | — | — | — |
| 8 | 192.45 | — | — | — | — |
| 2 | 1/12150 of the stock solution | — | — | — | — |
| 3 | 1/8403 of the stock solution | — | — | — | — |
| RBV | >2000 | 2.06 | 970.87 | 6.17 | 324.15 |

Note:
(1) "—" indicates that the max nontoxic dose of a sample did not have the activity against influenza A virus or influenza B virus.
(2) $TC_{50}$: the concentration of 50% toxicity of an agent; $IC_{50}$: the concentration of an agent with 50% inhibition of a virus; SI: selection index, $SI = TC_{50}/IC_{50}$.

The results shows that Compound 20 had the activity but the activity is not potent.

Example 8

Screening for the Agents Against Herpes Virus

Materials and Methods

Experimental samples: The stock solutions were prepared by dissolving Compounds 3-8, 14, 17, 19, 20, 21, 43 and Curcumol E in PBS or absolute alcohol, respectively, sterilized with a 0.45 μm filter, and stored away from light at 4° C. until use.

Virus and cells: oral membrane herpes virus (VSV), and 293, BHK cell lines were stored in liquid nitrogen by the Hepatitis & Gene Therapy research group of Wuhan Virus Institute of Chinese Academy of Sciences. Cells were grown in the DMEM medium supplemented with 10% fetal bovine serum (Gibico) in a $CO_2$ incubator at 37° C.

Preparation of Virus and Test of the Titer: Bhk Cells were Infected with VSV to propagate the virus. After 2-3 days, the cells were centrifuged, and the supernatant was collected. The titer of the virus was measured with the $TCID_{50}$ method, and the virus were stored away from light at −80° C. until use.

Screening for the agents: The 293 cells were counted and $1.5×10^4$ cells/well were seeded into a 96-well plate. After incubation overnight in an atmosphere of $CO_2$ at 37° C., each of the experimental samples in a given concentration was added to the cells. The cells were infected with VSV of $MOI=5×10^{-3}$. A negative control and a positive control were also included. The cytopathy were observed 12 hrs and 24 hrs after infection, and photographed with a digital photographer.

Results: Cytopathy and cell status 24 hrs after infection are shown in Table 13.

TABLE 13

Primary screening for the sample against herpes virus

| No. | concentration (μg/ml) | Cytopathy and cell status Sample + VSV | Sample |
|---|---|---|---|
| Compound 3 | 200 | Cytopathy | Normal |
| Compound 4 | 200 | Cytopathy | Good |
| Compound 5 | 200 | Cytopathy | Good |
| Compound 6 | 200 | Cytopathy | Good |
| Compound 7 | 200 | Cytopathy | Good |
| Compound 8 | 200 | Cytopathy | Good |
| Compound 14 | 200 | Cytopathy, poor | Poor |
| Compound 17 | 200 | Cytopathy | Good |
| Compound 19 | 200 | Cytopathy | Apoptotic |
| Compound 20 | 200 | Cytopathy | Good |
| Compound 21 | 200 | No remarkable cytopathy | Normal |
| Compound 43 | 200 | Cytopathy, Comparatively poor | Comparatively poor |
| E | 200 | Cytopathy, Comparatively poor | Comparatively poor |
| VSV | MOI = 0.005 | Cytopathy | Cytopathy |
| PBS + medium | 1% | Cytopathy | Good |
| alcohol + medium | 1% | Cytopathy | Good |

Cytopathy and cell status 12 hrs after partial infection: Since the concentration used was high (200 μg/ml), which leaded into a high toxicity to the cells, we decreased the concentration of the sample (50 μg/ml) in the following screening experiments. The results are shown in the following Table 14:

| No. | Concentration (μg/ml) | Cytopathy and cell status Sample + VSV | Sample |
|---|---|---|---|
| 14 | 50 | Cytopathy | Good |
| 43 | 50 | Cytopathy | Good |
| E | 50 | Cytopathy | Good |
| VSV | MOI = 0.005 | Cytopathy | Cytopathy |
| PBS + medium | 1% | Cytopathy | Good |
| Alcohol + medium | 1% | Cytopathy | Good |

Cytopathy and status of the cells treated with the primarily screened samples 12 hrs and 24 hrs after infection The results of the first round of the primary screening indicates that Compound 21 (among the 13 samples) had some activities against VSV. Further screening experiments were performed on Compound 21 at different concentrations. The results are as follows:

| No. | Concentration (μg/ml) | Cytopathy and cell status | | |
|---|---|---|---|---|
| | | Sample + VSV | | cell status of |
| | | 12 h | 24 h | 12 and 24 h |
| Compound 21 | 12.5 | Cytopathy | Cytopathy | Good |
| | 25 | Cytopathy | Cytopathy | Good |
| | 50 | Cytopathy of most cells | Cytopathy | Good |
| | 100 | Cytopathy of some cells | Cytopathy | Good |
| | 200 | No significant cytopathy | Cytopathy of some cells | Normal |

The results shows that Compound 21 in a concentration of 200 μg/ml had the activity against VSV.

Example 9

Screening for the Activity Against Hepatitis B Virus (HBV)

1. Materials and Methods 1.1 Experimental samples: The stock solutions were prepared by dissolving Compounds 6, 16, 14, 2, 3, 24, 17, 20, 33, 25, 47, 21 and Curcumol in PBS or absolute alcohol, respectively, sterilized with a 0.45 um filter, and stored away from light at 4° C. until use.

1.2 Virus and cells: HBV recombinant Baculovirus (vAcG-FPHBVc), sf9 and HepG2 were stored in liquid nitrogen by the hepatitis and gene therapy research group of Wuhan Virus Institute of Chinese Academy of Sciences. Cells were grown in the DMEM medium supplemented with 10% fetal bovine serum (Gibico) in a $CO_2$ incubator (FORMA) at 37° C.

1.3 Preparation of virus and test of the titer: The sf9 cells were infected with vAcGFPHBVc to propagate the virus. After 3 days, the cells were centrifuged, and the supernatant was collected. The titer of the vAcGFPHBVc virus was measured with the $TCID_{50}$ method, and the virus were stored away from light at −80° C. until use.

1.4 Measurement of HBV e antigen (ELISA method): briefly as follows:

1. The plate and reagents were balanced at 37☐ for 30 mins, the samples to be tested were balanced at room temperature for 30 mins;

2. 50 μl of test sample was added into each well. Two well was included as the negative and positive control, respectively, to which one drop of the negative control or positive control was added. There was also one well as the blank control;

3. One drop of the enzyme-conjugate was added to each well (except the blank well) and then mixed. The plate was covered, and incubated at 37☐ for 30 mins;

4. The plate was washed by a plate-washing machine, and dried after 5 times of washing;

5. One drop of individual Developer A and individual Developer B were respectively added into each well and mixed. The Plate was covered, and incubated at 37☐ for 15 mins;

6. One drop of stopping buffer was added into each well and mixed;

7. The results were read on a Enzyme-linked Detector at 450 nm, and normalized for results of the blank well.

HBV e antigen diagnostic kit was commercially obtained from Shanghai Shiye Kehua Biotechnology Co. LTD.

1.5 Screening for the agents: The HepG2 cells were counted and $1.5 \times 10^4$ cells/well were seeded into a 96-well plate. After incubation overnight in an atmosphere of $CO_2$ at 37° C., each of the experimental samples in a given concentration was added to the cells. After incubation at 37☐ for 24 hrs, the HepG2 treated with the samples were infected with vAcGFPHBVc of 100 MOI. A negative control and a positive control were also included. Four days after infection, the growth of the cells were observed, and the HBV e antigen in the supernatant was measured with the HBV e antigen diagnostic kit.

2. Results 2.1 Results of the HBV e antigen

The primary screening excluded the influence of the agents to the cells. The results primarily indicates that Compound 6, 16 and 2 amongst 13 samples had the activity against HBV.

| No. | Concentration (μg/ml) | Cell status | $OD_{450}$ of HBeAg | (Value of the positive control − Measured Value) Value of the positive control × 100% |
|---|---|---|---|---|
| 6 | 200 | Normal | 0.126 | 93.42723 |
| 16 | 200 | Normal | 0.502 | 73.81325 |
| 14 | 200 | Poor | 0.053 | 97.23516 |
| 2 | 200 | Normal | 0.607 | 68.33594 |
| 3 | 200 | Normal | 2.61 | −36.1502 |
| 24 | 200 | Normal | 2.387 | −24.5179 |
| 17 | 200 | Poor | 0.073 | 96.19197 |
| 20 | 200 | Normal | 2.201 | −14.8148 |
| 33 | 200 | Poor | 0.068 | 96.45279 |
| Curcumol | 200 | Normal | 2.654 | −38.4455 |
| 25 | 200 | Poor | 2.527 | −31.8206 |
| 47 | 200 | Poor | 0.365 | 80.95983 |
| 21 | 200 | Retarded growth | 0.137 | 92.85342 |
| + | | Normal | 1.917 | |
| − | | Normal | 0.057 | |

FIG. 1 shows the measured $OD_{450}$ value of the HBV e antigen sample, wherein the X-axis represents the No. of the test sample, which corresponds to the compounds of the present invention as follows:

| No. in FIG. 1: | 1 | 2 | 3 | 4 | 5 | 6 | 7 | A | B | C | D | E | F |
|---|---|---|---|---|---|---|---|---|---|---|---|---|---|
| No. of the compounds | 6 | 16 | 14 | 2 | 3 | 24 | 17 | 20 | 33 | Curcumol | 25 | 47 | 21 |

POSITIVE means the positive control, and NEGATIVE means the negative control.

Figure 2:
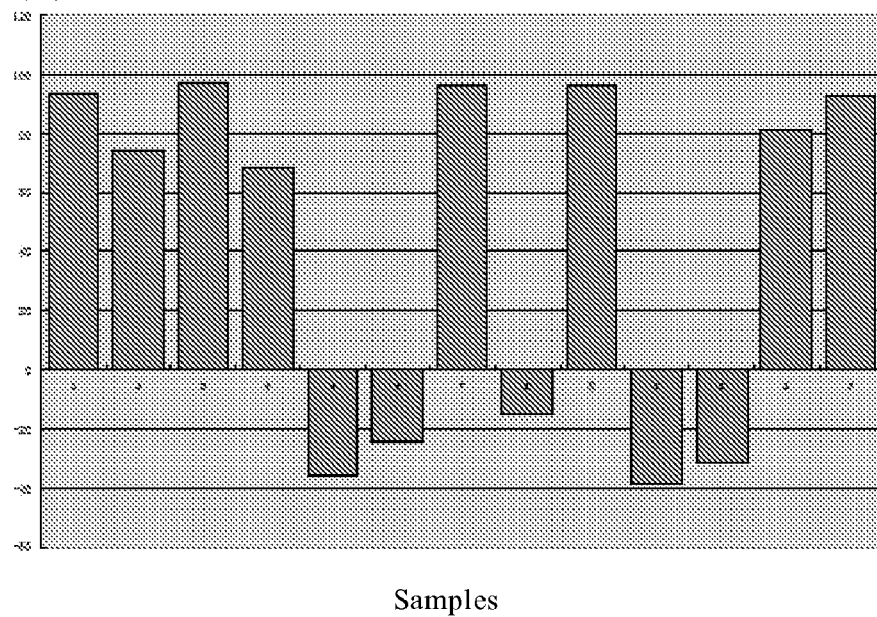
FIG. 2 shows the decreased percent ages of HBeAg sample relative to that of the positive control, upon treatment with curcumol and the compounds according to this invention.

FIG. 2 shows the decreased HbeAg by percent of the samples relative to that of the positive control. The numbering of FIG. 2 is identical with that of FIG. 1.

We claim:

1. A compound or a pharmaceutically acceptable salt thereof, wherein said compound comprising: a curcumol molecule modified by chemical groups Y or $R^1$ as shown in formula I:

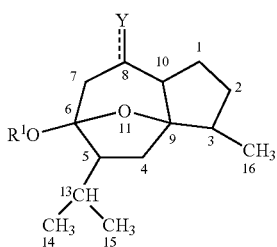

wherein, the chemical group $R^1$ is selected from the group consisting of R, RCO, $HO_3S$, acyl of coffeic acid, gambogic acid, isogambogic acid, neogambogic acid and glycyrrhizic acid;

Y is selected from the group consisting of $Y^1NY^2$, $Y^1CONY^2$, =$CHR^2$, —$CH_2R^2$,

—OH and —OR, wherein $Y^1$ is H or $C_{1-8}$, $Y^2$ is a $C_{1-8}$ heterocycle selected from the group consisting of

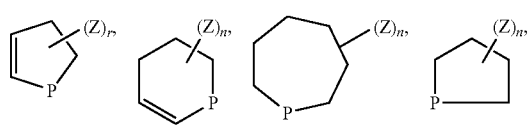

or 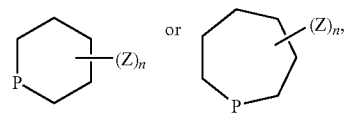

wherein P is S, O or N, Z is selected from the group consisting of H, hydroxy group, saturated or unsaturated linear $C_{1-6}$ hydrocarbon group, saturated or unsaturated branched $C_{3-6}$ hydrocarbon group, n=1-3, R is selected from the group consisting of H, saturated or unsaturated linear $C_{1-10}$ hydrocarbon group, saturated or unsaturated branched $C_{3-10}$ hydrocarbon group, $C_{3-10}$ hydrocarbon ether, $C_{3-10}$ hydrocarbon sulfide, saturated or unsaturated $C_{3-8}$ cyclic hydrocarbon group optically substituted by at least one substituent selected from the group consisting of nitro, sulfonic acid group, halogen atom, hydroxyl group and $C_{6-12}$ aryl group, $R^2$ is selected from the group consisting of F, Cl, Br, I, —OH, —OR, —$HSO_3$, —$NO_3$, RNH—, R'NR", pyridyl, pyrrolyl, imidazolyl, triazolyl, tetrazolyl, dioxazolyl, dioxadiazolyl, piperidyl,

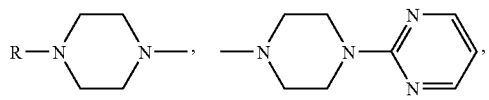

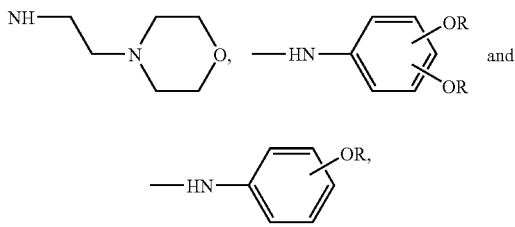

wherein, R' is selected from the group consisting of H, saturated or unsaturated linear $C_{1-10}$ hydrocarbon group, saturated or unsaturated branched $C_{3-10}$ hydrocarbon group, $C_{3-10}$ hydrocarbon ether, $C_{3-10}$ hydrocarbon sulfide, saturated or unsaturated $C_{3-8}$ cyclic hydrocarbon group optically substituted by at least one substituent selected from the group consisting of nitro, sulfonic acid group, halogen atom, hydroxyl group, $C_{6-12}$ aryl group and $H_2NRNH$, R" is selected from the group consisting of H, saturated or unsaturated linear $C_{1-10}$ hydrocarbon group, saturated or unsaturated branched $C_{3-10}$ hydrocarbon group, $C_{3-10}$ hydrocarbon ether, $C_{3-10}$ hydrocarbon sulfide, saturated or unsaturated $C_{3-8}$ cyclic hydrocarbon group optically substituted by at least one substituent selected from the group consisting of nitro, sulfonic acid group, halogen atom, hydroxyl group, $C_{6-12}$ aryl group and $H_2NRNH$.

2. The compound of claim 1, wherein the aryl group is selected from the group consisting of Ar—, $ArCH_2$—, $ArCH_2CH_2$—, and $CH_3ArCH_2CH_2$—, wherein Ar— is phenyl or phenyl group substituted with F, Cl, Br, I, nitro, sulfonic group or 1-3 hydroxy groups.

3. A compound or a pharmaceutically acceptable salt thereof, wherein said compound comprising formula III:

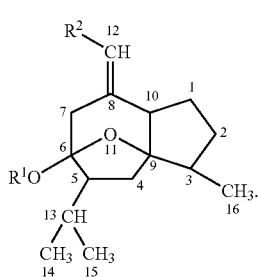

wherein $R^2$ is H, and $R^1$ is $HO_3S$, propionyl, butyryl, isobutyryl or benzoyl.

4. A compound or a pharmaceutically acceptable salt thereof, wherein said compound comprising formula III:

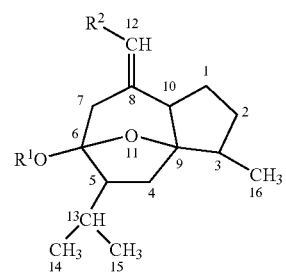

wherein $R^1$ and $R^2$ are as shown the following table:

| Name of the compounds | $R^1$ | $R^2$ |
|---|---|---|
| Curcumol butyrate | $CH_3CH_2CH_2CH_2C-$ | H |
| Curcumol isobutyrate | $(CH_3)_2CH_2CO-$ | H |
| Curcumol benzoate | ⌬—CO | H |
| Curcumol p-hydroxy aniline | H | —HN—⌬—OH |
| Curcumol p-hydroxy aniline hydrochloride | H | —HN—⌬—OH |
| Curcumol piperazine | H | HN⌬N— |
| Curcumol piperazine hydrochloride | H | HN⌬N— |
| Curcumol heterocyclyl ethylamine | H | NH—\—N⌬O |
| Curcumol heterocyclyl ethylamine hydrochloride | H | NH—\—N⌬O |
| 3,4-dihydroxy aniline | H | —HN—⌬(OH)(OH) |
| 3,4-dihydroxy aniline hydrochloride | H | —HN—⌬(OH)(OH) |

-continued

| Name of the compounds | R¹ | R² |
|---|---|---|
| Curcumol n-butyl amine | H | CH₃CH₂CH₂CH₂NH— |
| Curcumol n-butyl amine hydrochloride | H | CH₃CH₂CH₂CH₂NH— |
| Curcumol t-butyl amine | H | (CH₃)₃CNH— |
| Curcumol t-butyl amine hydrochloride | H | (CH₃)₃CNH— |
| Curcumol monobromide | H | —Br |
| Curcumol monohydroxy compound | H | —OH |
| Curcumol mononitrate | H | —NO₃ |
| Curcumol sulfonate | HSO₃— | H |
| Curcumol sodium sulfonate | NaSO₃— | H |
| Curcumol acrylate | CH₂=CHCO— | H |
| Curcumol diethanolamine | H | (CH₃CH₂)₂N— |
| Curcumol diethanolamine hydrochloride | H | (CH₃CH₂)₂N— |
| Curcumol methyl ether bromide | CH₃ | —Br |
| Curcumol methyl ether n-butyl amine | CH₃ | CH₃CH₂CH₂CH₂NH— |
| Curcumol methyl ether n-butyl amine hydrochloride | CH₃ | CH₃CH₂CH₂CH₂NH— |
| Curcumol ethyl ether nitrate | CH₃CH₂— | —NO₃ |
| Curcumol propionate | CH₃CH₂CO— | H. |

5. The compound of claim 1, wherein, Y . . . is a single bond, Y is —OH or —OR¹.

6. The compound of claim 1, wherein R¹ is H, Y is selected from Y¹NY², Y¹CONY², =CHR², —CH₂R²,

—OH.

7. A compound or a pharmaceutically acceptable salt thereof, wherein said compound comprising Formula II:

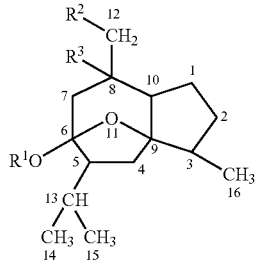

wherein R¹, R² and R³ are as shown the following table:

| Name of the compounds | R¹ | R² | R³ |
|---|---|---|---|
| Curcumol dibromide | H | —Br | —Br |
| Curcumol dinitrate | H | —NO₃ | —NO₃ |
| Curcumol dihydroxy compound | H | —OH | —OH |
| Curcumol monobromide without double bond | H | H | —Br |
| Curcumol monohydroxy compound without double bond | H | H | —OH |
| Curcumol mononitrate without double bond | H | H | —NO₃ |
| Curcumol p-hydroxy aniline without double bond | H | H | —HN—⟨C₆H₄⟩—OH |
| Curcumol p-hydroxy aniline hydrochloride without double bond | H | H | —HN—⟨C₆H₄⟩—OH |

-continued

| Name of the compounds | R¹ | R² | R³ |
|---|---|---|---|
| Curcumol bis (p-hydroxy aniline) | H | —HN—C₆H₄—OH | —HN—C₆H₄—OH |
| Curcumol bis (p-hydroxy aniline) hydrochloride | H | —HN—C₆H₄—OH | —HN—C₆H₄—OH |
| Curcumol bispiperazine | H | HN(piperazine)N | HN(piperazine)N |
| Curcumol bispiperazine hydrochloride | H | HN(piperazine)N | HN(piperazine)N |
| Curcumol piperazine without double bond | H | H | HN(piperazine)N |
| Curcumol piperazine hydrochloride without double bond | H | H | HN(piperazine)N |
| Curcumol methyl ether n-butyl amine without double bond | $CH_3$ | H | $CH_3CH_2CH_2CH_2NH$ |
| Curcumol methyl ether n-butyl amine hydrochloride without double bond. | $CH_3$ | H | $CH_3CH_2CH_2CH_2NH$ |

8. An anti-tumor pharmaceutical composition comprising a pharmaceutically effective amount of the compound or the pharmaceutically acceptable salt of any one of claim 1, 2, 3, 4, 5, 6 or 7, and a pharmaceutically acceptable excipient or an additive, wherein said compound inhibits tumor cell growth in vitro, wherein the tumor cell is selected from the group consisting of human histocytic lymphoma, human lung adenocarcinoma, human hepatic carcinoma, human mammary adenocarcinoma, human cervical carcinoma, human promyelocytic leukemia, and mouse Lewis lung carcinoma.

9. An anti-cancer pharmaceutical composition comprising a pharmaceutically effective amount of the compound or the pharmaceutically acceptable salt of any one of claim 1, 2, 3, 4, 5, 6 or 7, and a pharmaceutically acceptable excipient or an additive, wherein the cancer is selected from the group consisting of sarcoma, liver cancer, lung cancer and uterine cervix cancer.

10. An anti-virus pharmaceutical composition comprising a pharmaceutically effective amount of the compound or the pharmaceutically acceptable salt of any one of claim 1, 2, 3, 4, 5, 6 or 7, and a pharmaceutically acceptable excipient or an additive, wherein said compound inhibits viral enzyme activity or virus replication, said virus is selected from the group consisting of HIV, influenza A virus, infuluenza B virus, herpes virus and hepatitis B virus.

11. A method of inhibiting tumor cell growth comprising administering a pharmaceutically effective amount of the compound or the pharmaceutically acceptable salt of any one of claim 1, 2, 3, 4, 5, 6 or 7 to a mammal to inhibit the growth of tumor cell in the mammal.

12. The method of claim 11, wherein said tumor is selected from the group consisting of sarcoma, liver cancer, lung cancer and uterine cervix cancer.

13. A method of inhibiting tumor cell growth comprising administering a pharmaceutically effective amount of the compound or the pharmaceutically acceptable salt of any one of claim 1, 2, 3, 4, 5, 6 or 7 to a mammal, wherein the tumor cell is selected from the group consisting of human histocytic lymphoma, human lung adenocarcinoma, human hepatic carcinoma, human mammary adenocarcinoma, human cervical carcinoma, human promyelocytic leukemia, and mouse Lewis lung carcinoma.

14. A method of inhibiting virus growth comprising administering a pharmaceutically effective amount of the compound or the pharmaceutically acceptable salt of any one of claim 1, 2, 3, 4, 5, 6 or 7 to a mammal to inhibit viral enzyme activity or virus replication of said virus, wherein said virus is selected from the group consisting of HIV, influenza A virus, infuluenza B virus, herpes virus or hepatitis B virus.

* * * * *